United States Patent [19]
Ratner

[11] Patent Number: 5,843,643
[45] Date of Patent: Dec. 1, 1998

[54] SITE-SPECIFIC TRANSFECTION OF EUKARYOTIC CELLS USING POLYPEPTIDE-LINKED RECOMBINANT NUCLEIC ACID

[76] Inventor: Paul L. Ratner, 11 Ash St., Bar Harbor, Me. 04609

[21] Appl. No.: 199,608

[22] Filed: Feb. 22, 1994

Related U.S. Application Data

[63] Continuation of Ser. No. 838,964, Feb. 21, 1992, abandoned.

[51] Int. Cl.$^6$ .............................. C12Q 1/68; C12P 19/34; A61K 48/00; C07K 5/00
[52] U.S. Cl. ................................. 435/6; 435/91.1; 435/5; 514/44; 514/2; 536/24.5; 536/24.3; 536/23.1; 530/300; 530/350
[58] Field of Search .................................. 435/6, 91.1, 5; 514/44, 2; 536/24.5, 24.3, 23.1; 530/300, 350

[56] References Cited

U.S. PATENT DOCUMENTS 4,950,599  8/1990  Bertling ................................ 435/172.3

OTHER PUBLICATIONS

Cheng, S.T. et al., "A versatile method for the coupling of protein to DNA: synthesis of alpha–macroglobulin–DNA conjugates," *Nucl. Acids Res. 11*: 659–669 (1983).
Capecchi, M.R., "Altering the genome by homologous recombination," *Science 244*: 1288–1292 (1989).
Berkner, K.L., "Development of adenovirus vectors for the expression of heterologous genes," *Biotechniques 6*: 616–629 (1988).
Eglitis, M.A. and Anderson, W.F., "Retroviral vectors for introduction of genes into mammalian cells," *Biotechniques 6*: 608–614 (1988).
Vestweber, D. and Schatz, G., "DNA–protein conjugates can enter mitochondria via the protein import pathway," *Nature 338*: 170–172 (1989).
Jablonski, J., et al, "Preparation of oligonucleotidealkaline phosphates conjugates and their use as hybridization probes," *Nucl. Acids Res. 14*: 6115–6128 (1986).
Zuckermann, R.N., et al, "Site-selective cleavage of RNA by a hybrid enzyme," *J. Amer. Chem. Soc. 110*: 6592–6594 (1988).
Rosencranz et al, Experimental Cell Research 199:323–329, 1992.
Gutierrez et al, The Lancet 339:715–721, 1992.
Talmadge et al. Advanced Drug Delivery Reviews 10:246–299, 1993.
Freeman et al. Clinical Trials in Gene Therapy Advanced Drug Delivery Reviews 12:169–183, 1993.

*Primary Examiner*—W. Gary Jones
*Assistant Examiner*—Dianne Rees
*Attorney, Agent, or Firm*—Patrick D. Kelly

[57] ABSTRACT

A method and composition are disclosed for transfecting eukaryotic cells using a DNA segment coupled to a site-specific chromosome-binding polypeptide. The polypeptide-DNA conjugate is referred to herein as a polypeptide-linked-rDNA (PLR) molecule. One example of a PLR molecule comprises a DNA segment containing a nucleotide sequence from a normally functioning human gene, coupled by means of a covalent crosslinking reagent to a site-specific chromosome-binding polypeptide (such as a transcription regulating polypeptide that binds to a specific nucleotide sequence in chromosomal DNA). After the PLR molecule enters the cytoplasm of a cell, such as by electroporation, the chromosome-binding polypeptide enables transport of the PLR molecule through the cytoplasm and into the nucleus, using a nuclear localization sequence (NLS) domain of the polypeptide. Inside the nucleus, the polypeptide scans the chromosomes until it binds to a specific chromosomal binding site. This positions the DNA segment of the PLR molecule near a target sequence (such as a defective gene) in the chromosome. The desired DNA segment contained in the PLR molecule has sufficient nucleotide sequence homology with the target gene to enable a recombination event to replace the target gene sequence with the desired gene sequence.

13 Claims, 4 Drawing Sheets

SITE-SPECIFIC TRANSFECTION OF EUKARYOTIC CELLS USING POLYPEPTIDE-LINKED RECOMBINANT NUCLEIC ACID

This application is a continuation of U.S. patent application Ser. No. 07/838,964 filed Feb. 21, 1992 now abandoned.

BACKGROUND OF THE INVENTION

This invention is in the fields of biochemistry and molecular biology. It relates to a method of site-specifically transfecting eukaryotic cells using genetically engineered DNA.

In general, methods for incorporating (transfecting) nucleic acid into a eukaryotic chromosome are performed to study selected functions of nucleic acid, such as replication, recombination, gene regulation, and repair of mutations, or to cause the cells to express polypeptides which they did not express prior to transfection. In human gene therapy, normal genes are transfected to specifically compensate for the presence of inherited defective genes which cause disease. Examples of human hereditary diseases include sickle-cell anemia, familial hypercholesterolemia, hemophilia, and over 1,350 other presently incurable diseases, occurring on average, in one out of every 100 live births. These diseases, often referred to as birth defects or inborn errors, are discussed in various texts such as Stanbury 1983 (complete citations are provided below, before the claims).

In one method of obtaining a normal human gene for use in gene therapy, human tissue is homogenized and centrifuged, and the separated nuclei are extracted with organic solvents to isolate chromosomal deoxyribonucleic acid (DNA). As used herein, "chromosomal DNA" refers to DNA in the nucleus, and does not include DNA in cellular organelles such as mitochondria or chloroplasts. The double-stranded DNA (dsDNA) is fragmented using restriction endonucleases or sonication, and fragments are enzymatically incorporated (molecularly cloned) into a self-replicating dsDNA molecule, such as a bacterial plasmid (vector) which is used to transform a bacterial culture. Sufficient quantities of recombinant DNA can then be produced for identification, purification, and use of the specific human gene for gene therapy. Recombinant DNA technology is discussed in various texts such as Lewin 1990 and Sambrook et al 1989.

A basic requirement specific to gene therapy is the transfection of such recombinant DNA into human recipient cells. As used herein, "transfection" refers to the deliberate introduction of DNA from outside a cell into the cytoplasm or nucleus of the cell. This can be done, under the prior art, using any of several methods, discussed below. The subsequent step of incorporating transfected DNA into chromosomal DNA, by means such as homologous recombination, is usually referred to as chromosomal DNA integration (or simply integration). Transfection can allow the recombinant DNA to enter the cell nucleus and become integrated into a chromosome, so that the recombinant DNA can be replicated and passed on to progeny cells in the normal manner. Unless otherwise specified, cells containing transfected DNA are referred to herein as transfected cells, regardless of whether the DNA has become integrated into the chromosomal DNA.

Chemical Transfection Methods

One chemical method for transfecting DNA into the cytoplasm of a cell involves co-precipitation of dsDNA and cells with calcium phosphate; however, this is not efficient for linear dsDNA, which is generally considered the preferred cellular substrate for chromosomal DNA integration. The transfection of cells grown in diethylaminoethyl-dextran is useful for transient gene expression but produces high rates of unwanted mutations. The chemical entrapment of dsDNA within lipid vesicles allows the use of linear dsDNA, but it requires specific expertise, and the transfection frequency is too low for clinical use with many cell types. Entrapment of dsDNA within erythrocyte or bacterial membranes yields variable transfection efficiencies, but can introduce foreign antigenic polypeptides into human cells. These and other chemical methods of inserting nucleic acid into cells are described in various references such as Keown et al 1990.

Physical Transfection Methods

Various physical methods of transfection are also available. Direct microinjection of dsDNA into the nucleus of an individual cell is possible, but it is expensive, requires specialized expertise, and allows the transfection of only one cell at a time.

Another physical method, often called electroporation, involves the application of an electric pulse to cells grown in liquid suspension cultures, to generate transient permeability in the cell membranes. Macromolecules such as dsDNA and polypeptides can enter the cells during the period of membrane permeability. This method, and an electronic system which is used to carry it out using an electrode suspended above the surface of the liquid holding the cells, are described in U.S. Pat Nos. 4,663,292 (Wong and Wong, 1987) and 4,849,355 (Wong 1989), and equipment for carrying out this process is sold by Baekon, Inc. (Fremont, Calif.). Other electroporation systems which involve capacitor-type electrodes that are submerged into cell solutions are sold by suppliers such as Bio-Rad (Richmond, Calif.) and Invitrogen (San Diego, Calif.).

Microacceleration (also called "biolistics" by its inventors) involves coating dsDNA onto tiny particles (several micrometers in diameter) of a metal such as tungsten, and physically shooting the particles into cells using a particle gun. The equipment for carrying out this process is sold by the Biotechnology Systems division of DuPont Company (Wilmington, Del.). The process is described in U.S. Pat. No. 4,945,050 (Sanford et al 1990), and in articles such as Klein et al 1987 and Zelenin et al 1991.

Electroporation and microacceleration can both be used to insert macromolecules such as dsDNA or polypeptides into the cytoplasm of large numbers of cells. However, in only a relatively small percentage of the cells that are transfected by any of the chemical or physical methods mentioned above, can the inserted dsDNA become integrated into a chromosome. Also, in an even smaller percentage of such cells does the dsDNA become integrated into a specifically-targeted homologous region in chromosomal DNA.

Adenovirus Transfection Methods

Another class of transfection methods (in addition to the chemical and physical methods discussed above) involves the use of genetically engineered viruses to carry a desired nucleotide sequence of dsDNA. For example, a dsDNA carrying a human nucleotide sequence can be molecularly cloned within the dsDNA genome of an Adenovirus. Adenovirus vectors are discussed in references such as Berkner 1988, Ginsberg et al 1991, and LeMarchand et al 1992. Several human genes can be maintained under separate genetic control on a single adenoviral vector, and the engineered vector can be used to transfect tissue culture cells.

Large amounts of infectious adenoviral-human recombinant viruses are subsequently produced and used to infect human recipient cells. However, gene expression gradually declines so that infections must be repeated subsequently to maintain sufficient levels, a process which makes clinical use difficult. Adenoviruses can also cause pneumonia-like symptoms in mice, rats, and humans. Adenoviral vector transfection also cannot produce high levels of homologous integration into chromosomes, which renders it quite difficult to carry out effective gene therapy.

Retroviral Transfection Methods

The only method of human gene therapy which has been approved for clinical testing on human patients uses vectors derived from retroviruses. Retroviruses are a class of vectors which contain single-stranded RNA (ssRNA). A retrovirus must first attach its outer lipopolypeptide coating to a eukaryotic cell membrane in order to enter the cell. Following penetration and uncoating, the retroviral ssRNA can then be translated by the cell's ribosomes for the synthesis of retroviral polypeptides. One of the polypeptides encoded by the ssRNA is reverse transcriptase, an enzyme which uses the retroviral ssRNA as a template to generate a corresponding (complementary) dsDNA transcript, which can be inserted into the chromosomes of the infected cells. Retroviruses can infect most eukaryotic cell types, and virtually all cells in a culture usually become infected; this allows gene therapy of rare cell types, such as T-cell infiltrating lymphocytes (TIL), and self-replicating human stem cells (SC).

Recombinant DNA technology allows retroviruses to be used in gene therapy by the incorporation of molecularly cloned human genes into the retroviral genome. The deletion and inactivation of retroviral regulatory and structural genes are also required, to greatly reduce virulence and tumorigenicity. If desired, several different genes can be incorporated into and can be independently regulated on a single retroviral transfection vector. The construction of retroviral transfection vectors, and their use in gene therapy, are reviewed in various references such as Eglitis and Anderson 1988, and McLachlin et al 1990.

Despite the versatility and efficiency of retroviruses, they suffer from several major limitations. For example:

1. Their small genome (usually less than ten thousand nucleotide base pairs, 10 kb) allows cloning of inserts only up to about 7 kb). This is insufficient for the cloning of larger genes, as can be found especially in genomic DNA.

2. The incorporation of human genes deletes retroviral structural and regulatory genes required for infection. Therefore, for use in gene therapy, it is necessary to provide these missing gene functions by transfecting the dsDNA of defective retroviral vectors into tissue culture cells, usually of rodent origin, which already contain a different class of retroviral genome that can provide the missing gene functions and thereby produce infectious transfection vectors. This process is expensive, laborious, and produces unwanted cell culture contaminants which must be removed before the retroviral transfection vectors can be used in human gene therapy.

3. Retroviral vectors can recombine with the highly homologous, endogenous retroviral-like sequences which exist in all human cells. Since tissue-specific gene expression has been observed among these endogenous human sequences, they can also replace functions missing on retroviral vectors, and vice-versa. This recombination and replacement creates the risk of generating pathogenic strains from the retroviral vectors and the endogenous human retrovirus-like sequences. Also, since most retroviral transfection vectors are constructed from avian and rodent tumor viruses, there is the further possibility that recombination with endogenous retroviruses would complicate the use of animals for basic research and for safety testing of transfection vector constructs before their use in human gene therapy.

4. There is also the possibility that the presence of regulatory sequences on retroviral vectors would compete for nuclear regulatory polypeptides such as AP-1, Sp1, and USF, thereby disrupting normal genetic expression of both the transfected human genes, and of other human chromosomal genes.

5. Unreliable genetic expression has reportedly resulted when complementary dsDNA transcripts of genes (such as human beta globin genes) were molecularly cloned on retroviral vectors and used to transfect mammalian cells; see McLachlin et al 1990.

6. Retroviral-based transfection very rarely inserts a human gene into its corresponding chromosomal site. The frequency of such site-specific incorporation has been estimated to range from only about one in ten-thousand cells, to about one in a million cells. Therefore, in the overwhelming majority of transfected cells, the defective gene(s) will remain. Continued expression of certain types of defective genes, as in sickle-cell anemia, can be pathogenic despite the presence of the normal transfected genes.

7. The rarity of site-specific integration when using retroviral vectors also positions transfected genes between unrelated chromosomal sequences. This can cause the transfected genes to suffer from low expression levels and abnormalities in the timing and cellular specificity of their genetic regulation. These potentially pathogenic results are uncontrollable and unpredictable.

8. Retroviral and human genes incorporated into unnatural chromosomal locations can also be pathogenic by causing the inappropriate expression, or the inactivation, of adjacent chromosomal genes. In addition, retroviral transfection can cause unwanted deletions, insertions, substitutions, frameshifts, unscheduled replication, and translocation of the transfected and adjacent chromosomal genes. Hence, retroviruses are mutagenic; they are actually used to produce various types of genetic alterations in experimental animals.

Therefore, it would be clinically useful to have an efficient method of transfecting human and other eukaryotic cells that does not utilize retroviral vectors or any other type of viral vector. Preferably, such a method should allow genes to be inserted into chromosomes in a site-specific manner, so that they would enable gene replacement therapy. This would help ensure that the inserted gene is properly expressed with regard to timing, level of expression, and cell specificity; it would also help ensure that the integration of the transfected gene does not alter the structure or function of normal chromosomal genes in the transfected cells (Friedmann 1989).

Polypeptides Coupled to dsDNA

Another approach to transfection was reported in Cheng et al 1983. This method involved chemically coupling dsDNA to a polypeptide. Cheng et al used a human plasma polypeptide, alpha$_2$ macroglobulin ($\alpha_2$M) which binds specifically to a receptor polypeptide on the outer membrane of certain types of human cells. This binding initiates endocytosis, a process wherein both the receptor polypeptide and the $\alpha_2$M are brought into the cytoplasm of the cells.

In the process reported by Cheng et al, $\alpha_2$M was first derivatized with 2-iminothiolane, to add disulfide (—S—

S—) groups to the surface of the polypeptide. Then, in two sets of experiments, two different genes were coupled to the $\alpha_2$M. One of the genes (8.2 kb) encoded the thymidine kinase enzyme from Herpes simplex virus type 1. The other gene encoded a bacterial gene, chloramphenicol acetyltransferase (2.2 kb) from *Escherichia coli*, which inactivates an antibiotic, chloramphenicol. Approximately 10 to 25 deoxyguanine (dG) nucleotides were added to the 3-hydroxyl termini of each gene by an enzyme, terminal transferase. This allowed the single-stranded dG chains to react with N-acetyl-N'-(pglyoxylylbenzoyl)cystamine to introduce, in a reducing (acidic) environment, several mercapto groups (—SH) per molecule. The dsDNA and the $\alpha_2$M polypeptide were then reacted in an oxidizing (basic) environment, causing the disulfide groups on the polypeptide to react with the mercapto groups on the dsDNA, forming new disulfide (—S—S—) bonds, thereby producing polypeptide-dsDNA conjugate molecules.

When these conjugates were contacted with cells that expressed $\alpha_2$M receptors in tissue culture, the conjugates underwent endocytosis into the cellular cytoplasm. In effect, the method developed by Cheng et al offered a method of inserting dsDNA into the cytoplasm of certain types of cells; the result was essentially comparable to electroporation, microacceleration, calcium phosphate precipitation, and other methods mentioned above.

Once internalized by the cells, most of the bound polypeptide-dsDNA conjugates reported by Cheng et al would be routinely transported to the eukaryotic cell's degradative organelles, the lysosomes. The reducing environment within the lysosomes would cleave the disulfide bonds used for coupling the polypeptide to the dsDNA. Although this might free a portion of the dsDNA for subsequent migration to the nucleus, is far more likely that the lysosome would digest and damage the dsDNA. Similarly, if any conjugates escape or avoid the lysosomes, they would be cleaved enzymatically in the cytoplasm to release the dsDNA from the polypeptide, and the dsDNA is likely to be either enzymatically degraded in the cytoplasm or the nucleus, or transported to the lysosome for acidic digestion. It is also not possible for an intact conjugate containing the $\alpha_2$M polypeptide, a large polypeptide with a molecular weight of approximately 720,000 (720 kDa), to penetrate the pores of the nuclear membrane.

Accordingly, the transfection frequency would be very low, since much of the dsDNA would be degraded or mutated, and chromosomal integration would not be site-specific.

One other report which describes polypeptide-dsDNA coupling and transport involved the mitochondria, the eukaryotic cell's primary energy-producing organelles. This work is reported in Vestweber and Schatz 1989. They used a chimeric gene to synthesize a fusion polypeptide that contained the first 24 amino acids of a yeast enzyme, cytochrome oxidase subunit IV, which is normally transported into yeast mitochondria. In the fusion polypeptide, this mitochondrial localization sequence was coupled to the amino acid sequence of a murine enzyme, dihydrofolate reductase. The fusion polypeptide, expressed in *E. coli*, was then chemically coupled to a 24 base segment of single-stranded DNA (ssDNA) using a chemical crosslinker, maleimidobenzoyl-N-hydroxysuccinimide ester. This polypeptide-ssDNA conjugate was hybridized to a second strand of ssDNA with a complementary nucleotide sequence, and the resulting dsDNA-protein conjugate was added in vitro to isolated yeast mitochondria. About 5–10% of the conjugate was transported into mitochondria.

Mitochondrial polypeptide import, which is described in various references such as Hartl and Neupert 1990, is substantially different from the processes by which molecules pass through nuclear membranes. In mitochondrial transport, individual localization sequences are each specific for the they are almost always located at the N-terminus of a polypeptide, and are cleaved after entry, so that import is only one-directional. Mitochondrial import also requires mitochondrial membrane polypeptides which interact specifically with polypeptides destined for entry into mitochondria. In addition, most imported polypeptides are unfolded (denatured), a process which would permanently inactivate nearly any nuclear polypeptides, and globular polypeptides larger than only 6 kDa cannot enter at all. Therefore this experiment was not designed or suited for gene therapy, but rather to suggest a mechanism by which nuclear dsDNA might naturally enter the mitochondrion.

Various other types of polypeptide-dsDNA conjugants have also been created for purposes that are unrelated and unsuited to cell transfection or gene therapy. For example, the enzyme alkaline phosphatase (AP), which causes a chromogenic reaction under certain conditions, can be coupled to an ssDNA probe which can be used for detection of a DNA hybridization reaction in vitro. This type of DNA analysis and the techniques used to couple enzymes to ssDNA probes are described in references such as Jablonski et al 1986. In addition, several types of nuclease-ssDNA conjugates have been created to cut ssDNA in vitro, as described in Zuckermann and Schultz 1988; most of these have been created using a disulfide coupling method that is not stable in vivo, and they are not related or suited to cell transfection or gene therapy.

One object of this invention is to construct a molecular conjugate containing a DNA segment coupled to a selected chromosome-binding polypeptide, by reacting both with a crosslinking reagent that can produce covalent or non-covalent bonds that are sufficiently stable in the cytoplasm and nucleus to allow efficient site-specific transfection of eukaryotic cells.

The method and the molecular conjugates of this invention have a number of important advantages, including: (1) they can facilitate the site-specific recombination of their own genomic or complementary DNA into eukaryotic chromosomes; (2) they need not contain any bacterial, viral, non-homologous eukaryotic, or other non-human DNA sequences; (3) they can be constructed and purified precisely, safely, and reproducibly; (4) the final product can be tested for safe and effective therapeutic use, using standard biochemical assays, laboratory animals, or tissue culture cells; (5) they can be used in conjunction with a variety of different transfection methods such as electroporation or microinjection; (6) they can be used for the transfection of cells by a large variety of genes, and by several genes simultaneously; (7) they can be used to transfect a wide variety of eukaryotic cell types; (8) they can enable site-specific mutation; (9) they can facilitate the industrial synthesis of polypeptides by human or other eukaryotic cells; and (10) they can enable improved and effective gene therapy for defective chromosomal genes in human patients and other eukaryotes.

SUMMARY OF THE INVENTION

A method and composition are disclosed for transfecting eukaryotic cells using a DNA segment coupled to a site-specific chromosome-binding polypeptide. The polypeptide-DNA conjugate is referred to herein as a polypeptide-linkedrDNA (PLR) molecule. One example of a PLR molecule comprises a DNA segment containing a nucleotide sequence from a normally functioning human gene, coupled by means of a covalent crosslinking reagent to a site-specific chromosome-binding polypeptide (such as a transcription regulating polypeptide that binds to a specific nucleotide sequence in chromosomal DNA). After the PLR molecule enters the cytoplasm of a cell, such as by electroporation, the chromosome-binding polypeptide enables transport of the PLR molecule through the cytoplasm and into the nucleus, using a nuclear localization sequence (NLS) domain of the polypeptide. Inside the nucleus, the polypeptide scans the chromosomes until it binds to a specific chromosomal binding site. This positions the DNA segment of the PLR molecule near a target sequence (such as a defective gene) in the chromosome. The desired DNA segment contained in the PLR molecule has sufficient nucleotide sequence homology with the target gene to enable a recombination event to replace the target gene sequence with the desired gene sequence.

DETAILED DESCRIPTION OF THE PREFERRED EMBODIMENT

Figure 1:
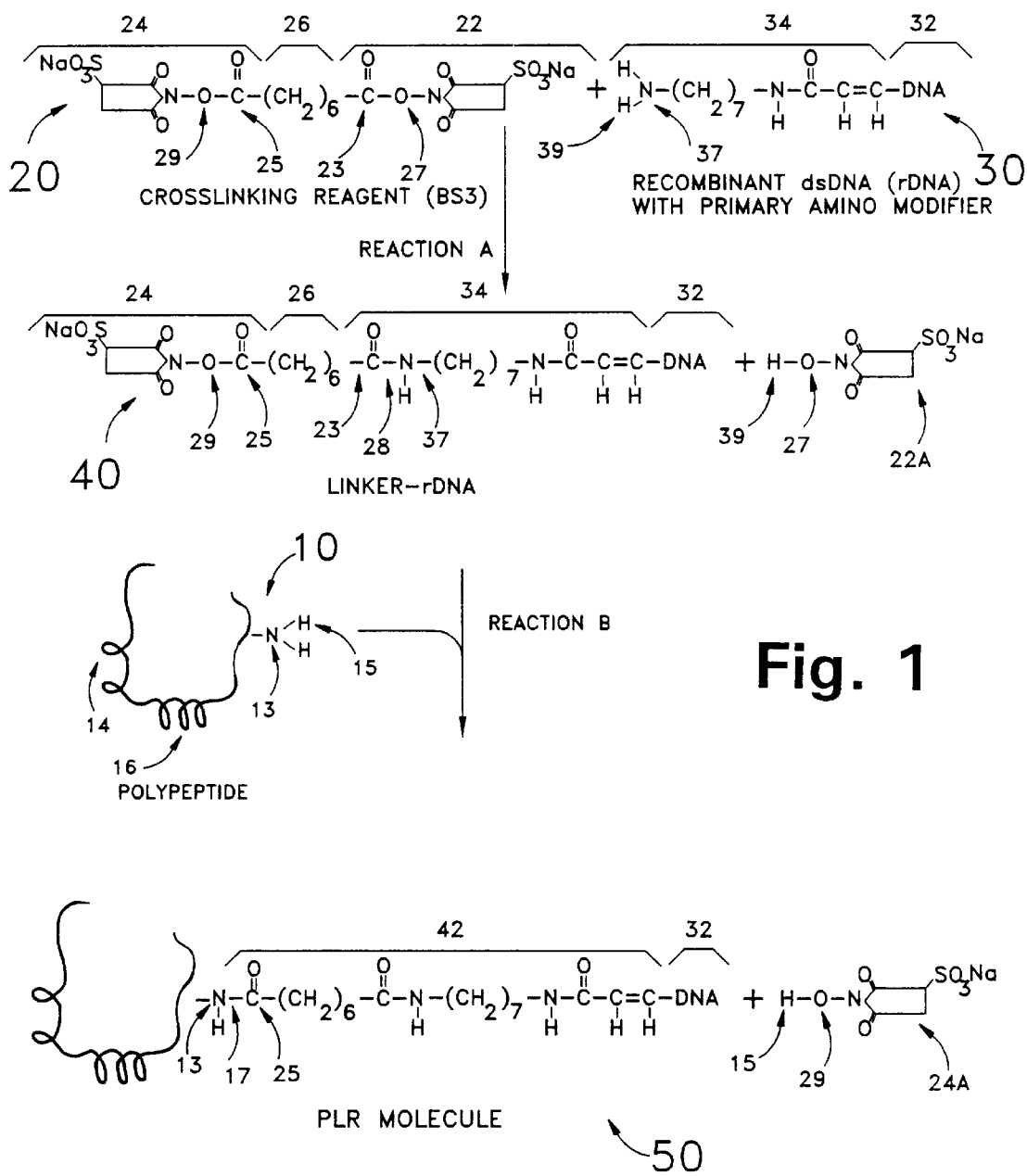
FIG. 1 is a schematic representation depicting the construction of a PLR molecule comprising three components: (a) polypeptide 10, which is a chromosome-binding polypeptide capable of entering a nucleus and binding to a specific site in chromosomal dsDNA; (b) a crosslinking reagent 20; and (c) a recombinant DNA molecule 30 that has been modified to facilitate crosslinking and which contains a DNA sequence that is to be recombined into a chromosome of a target cell. These components are covalently bonded together to form a "Polypeptide-Linked-Recombinant" (PLR) molecule 50, shown in the bottom of the figure.

This invention relates to a molecular conjugate and to a method of using this molecular conjugate to genetically transform eukaryotic cells. The molecular conjugate is referred to herein as a "Polypeptide-Linked Recombinant" (PLR) molecule 50. The three components that can be crosslinked together to create one preferred embodiment of the PLR molecule 50 are shown in FIG. 1.

One component is a selected eukaryotic polypeptide 10 which binds to a specific site on chromosomal DNA. This polypeptide has a reactive group, such as an amino group 13 which preferably is a primary amino group as shown, which facilitates bonding of the polypeptide 10 to a crosslinking reagent 20.

A second component is a crosslinking reagent 20 which couples the chromosome-binding polypeptide 10 to a recombinant dsDNA segment 30, preferably using a covalent linkage.

A third component is a recombinant DNA (rDNA) segment 30 which has been modified by the incorporation of a reactive group, such as a primary amino nitrogen atom 37, to enable the rDNA component 30 to be covalently coupled to the crosslinking reagent 20.

Further descriptions of these components, methods of coupling them together to form the PLR molecule 50, and the use of the PLR molecule 50 to facilitate the site-specific transfection of eukaryotic cells, will be presented below under various headings.

The Polypeptide (P) Component: A Site-Specific Chromosome-Binding Polypeptide

The polypeptide portion of a PLR molecule comprises a site-specific chromosome-binding polypeptide. As used herein, "chromosome" refers to chromosomal DNA, and to complexes containing both chromosomal DNA and nuclear polypeptides that are bound to chromosomal DNA. Various chromosome-binding polypeptides are known, as discussed below; however, only some of these can be regarded as "site-specific chromosome-binding polypeptides" which bind to chromosomal DNA at specific sites in a non-random configuration. For convenience, "site-specific chromosome-binding polypeptides" which meet the necessary criteria for use as described herein are referred to by the acronym, SSCBP's.

Except in certain situations (such as topoisomerase II and ATBP polypeptides, mentioned below), site-specific binding requires a particular nucleotide sequence in the chromosomal DNA at the site being bound by the polypeptide. In addition to requiring a particular sequence, binding can also require the presence of flanking nucleotide sequences, or a particular structure (such as a chromosomal dsDNA loop, a hairpin loop, a 4-way junction, or a cruciform (cross-like) arrangement at or near the site). Such structures (discussed in references such as Lewin 1990 and Bianchi et al 1989) are usually called higher-order structures, to distinguish them from dsDNA in its simplest coiled or nucleosome configuration. These natural phenomena involving flanking nucleotide sequences and higher-order chromosomal structures can enable SSCBP's to bind at appropriate locations without binding to similar nucleotide sequences that occur in other locations where binding of the polypeptides would be undesirable.

One major class of chromosome-binding polypeptides that exhibit low levels of site specificity, and which therefore are not preferred for use in PLR molecules as described herein, comprises histones such as H2A, H2B, H3, and H4, which are normally bound to chromosomal DNA as octamer complexes. Chromosomal DNA is normally wound around these octamers, and the resulting polypeptide-DNA structure is referred to as a nucleosome. The additional binding of another histone polypeptide (called H1) to a nucleosome forms a somewhat tighter polypeptide-DNA structure called chromatin. These structures and polypeptides are discussed in reference works such as Alberts et al 1989. Although histones generally are not preferred for use in this invention, they can be tested as described herein to determine whether they can enable sufficient homologous recombination frequencies.

A different class of proteins called "high mobility group" (HMG) polypeptides have intermediate nucleotide site specificity between low-specificity histones, described above, and the polypeptides shown in Table 1, which have a high preference for nucleotide binding at specific sites. Some HMG polypeptides (such as HMG 14 and HMG 17) are often bound to chromosomes at specific sites being replicated or transcribed (Alberts et al 1989). Such polypeptides might be useful in some situations for facilitating site-specific homologous recombination as described herein, if no other polypeptides with a higher level of site specificity are available for targeting a particular gene or region. In addition, as noted below, some HMG polypeptides such as HMG I(Y) (Thanos and Maniatis 1992) have a substantially higher level of site specificity than HMG 14 or HMG 17, and may approach the efficiencies of the polypeptides listed in Table 1 if used in itself. These site-specific chromosome-binding strategies can be commonly observed in another type of chromosomal polypeptide collectively known as transcription factor polypeptides (Alberts et al 1989).

The analogies among chromosome-binding polypeptides can also extend, in particular, to the site-specific nature of this binding, which is another characteristic of the polypeptide (P) component in this invention. This site-specificity can include binding to a specified nucleotide sequence such as 5'-GGGAAATTCC (SEQ ID NO:1), which is recognized by both a transcription factor known as NF-kappaB, and by a high mobility group polypeptide, HMG I(Y). An example of another transcription factor polypeptide is HNF1, which binds in rat hepatocytes to the less specific nucleotide

TABLE 1

REPRESENTATIVE DNA-BINDING PROTEINS
(Human origin unless noted)

| Name of protein | Gene bound by protein | Publication |
|---|---|---|
| AP-2 | Metallothionine IIA | Johnson & McKnight 1989 |
| Glucocorticoid receptor | Growth hormone | " |
| IRF-1 | Beta interferon | " |
| Oct-2 | Immunoglobulin heavy chain | " |
| Sp1 | Human immunodeficiency virus | " |
| SRF | c-fos oncogene | " |
| Thyroid hormone receptor | Growth hormone | " |
| CREB | Somatostatin | Singh et al 1989 |
| NF-kB | Human immunodeficiency virus | " |
| YB-1 | Major histocompatibility II | " |
| GATA-1 | Beta globin | Trainor et al 1990 |
| GCF | Epidermal growth factor | Kageyama & Pastan 1989 |
| GHF-1 | Growth hormone | Bodner et al 1989 |
| ITF-1 | Beta interferon | Zinn and Maniatis 1986 |
| LF-B1 | Alpha-1 antitrypsin | Frain et al 1989 |
| PRDII-BF1 | Beta interferon | Fan and Maniatis 1990 |
| TCF-1 | CD3-epsilon | van der Wetering 1991 |
| TFE-3 | Immunoglobulin heavy chain | Beckmann et al 1990 |
| Derived from mouse cells: | | |
| MyoD1 | Creatinine kinase | Johnson & McKnight 1989 |
| GPE1-BP | G-CSF | Nishizawa et al 1991 |
| Pu.1 | Major histocompatibility II | Klemsz et al 1990 |

PLR molecules as described herein.

Other types of polypeptides bind primarily to chromosomal structures; examples include topoisomerase II (Razin et al 1991), which binds to chromosomal loops, and ATBP (von Kries et al 1991), which binds to AT-rich regions where chromosomes bind to nuclear membranes. In addition, some transcription factor polypeptides can site-specifically bind to hairpin or cruciform structures (Ackerman et al 1993). Such polypeptides, most of which are not highly sequence-specific, can be regarded as site-specific, and can be evaluated as described herein for enabling homologous recombination; these may be especially useful for transfecting genes that do not have any known sequence-specific chromosome-binding polypeptides associated with such sites.

Site-specific binding of chromosomal polypeptides to the chromosomal DNA can thus include such variations as the direct binding of a single polypeptide to DNA. It can also include the specific binding of more than one identical or nonidentical polypeptide as a multimer, with each polypeptide also directly binding to the DNA. In addition, site-specific binding can include more than one identical or nonidentical polypeptide which binds as a multimer, but in binding not all of the polypeptides directly contact the DNA sequence GTTAATNATTAAC(SEQ ID NO:2) (where N is a variable that refers to any nucleotide), whereas the chromosomal enzyme topoisomerase II can bind at structural loops in chromosomes at a similar variable nucleotide sequence, GTN(A/T)A(T/C)ATTNATNN(G/A) (SEQ ID NO.:3), where either of the two nucleotides in parentheses can be present (Gasser and Laemmli 1987, Baumhueter et al 1988).

Site-specific binding is also demonstrated by the "Ets" family of transcription factor polypeptides. The consensus binding sequence, GGA(A/T), is very short, and this sequence must be flanked by additional nucleotide sequences, which may become associated with other transcription factor polypeptides. These flanking sequences, in conjunction with the above consensus sequence, determine the site-specificity and the affinity of binding of specific polypeptides in the Ets family (Janknecht and Nordheim 1993).

The transcription factor polypeptide GATA-1 also binds to a short nucleotide sequence, GAT. As in the Ets binding family, flanking nucleotide sequences govern the binding of GATA-1 to only a small number of binding sites (Merika and Orkin 1993, Whyatt et al 1993). Since a three base pair sequence will occur in random statistics every 64 nucleotides, such flanking effects are needed to limit GATA-1 binding to only a few preferred specific sites in human and mouse alpha-globin and beta-globin genes (Plumb et al 1989).

The transcription factor polypeptide Sp1 shows yet another aspect of site-specific binding to a short nucleotide sequence GGGCGG, since it can also bind to entirely different sequences in certain other species (such as NGGNGN in human cells that have been infected by papilloma viruses, and to CGCCCCGC in Drosophila). These data suggest that Sp1 forms polypeptide-polypeptide binding associations with other polypeptides to facilitate binding (Gloss and Bernard 1990, Kuton and Schwander 1993). In addition, binding of Sp1 to a non-canonical site GGTTGGACC in a human neurofilament gene was reported to require contact between Sp1 and a transcription factor polypeptide, Prox binding protein, since Sp1 could not bind to the above nucleotide sequence alone (Elder et al 1992). Flanking nucleotide sequences could create a particular chromosomal configuration which enables the transcription factor polypeptides Oct-1, Oct-2A, and Oct-2B to site-specifically bind to the site ATGCAAAT and also to CTCATGA (Kemler et al 1989).

The human transcription factor polypeptide SRY can site-specifically bind to a variable nucleotide sequence A/C) A(C/G)AAA(G/T). However, recognition of structural features such as the phosphodiester backbone of chromosomal DNA reportedly mediates this binding and produces a structural bend in the DNA. SRY also binds to 4-way junctions (i.e., regions where dsDNA crosses to overlap itself); this binding to junctions apparently does not have any nucleotide sequence specificity, yet SRY has a higher binding affinity for such junctions than for binding to the nucleotide sequence listed above (Ferrari et al 1992). Any sequence specificity of SRY binding, rather than reflecting direct contact with specific nucleotide sequences, is probably primarily concerned with topological structures of chromosomal DNA (King and Weiss 1993). Therefore, this transcription factor polypeptide demonstrates site-specific chromosomal binding. This is also true for a human transcription factor polypeptide, hUBF (Jantzen et al 1990) which recognizes no clear consensus nucleotide sequence, but which can bind site-specifically to GC-rich chromosomal regions of the ribosomal RNA genes.

The foregoing discussion provides several examples of chromosomal genes which effectively provide a range of levels for site-specific binding. Accordingly, if a chromosome-binding polypeptide which can exhibit a high degree of site specificity (such as the polypeptides listed in Table 1) is not known or available for use in a PLR molecule to alter a specific target gene, then alternate chromosome-binding polypeptides which have less site specificity (as described above) can be evaluated for use in the PLR molecules of this invention. This can determine whether these polypeptides can enable a sufficient level of the desired site-specific homologous recombination in a target gene.

As used throughout the remainder of this application, any reference to a chromosome-binding polypeptide refers to a site-specific chromosome-binding polypeptide, whether or not such polypeptide also has nucleotide sequence specificity; hence, the following discussion primarily concerns polypeptides which can bind to specific sequences of dsDNA.

Most eukaryotic dsDNA-binding polypeptides have two domains which are essential to their functioning and relevant to the subject invention. One such domain, usually called the "nuclear localization sequence" (NLS), is represented by callout number 14 in the figures. A polypeptide can contain more than one NLS (Picard and Yamamoto 1987). This domain facilitates the transport of the polypeptide into the nucleus. The other domain, depicted by callout number 16, is the dsDNA-binding domain. The functioning of each of these domains in the context of a PLR molecule is discussed below.

In nature, most dsDNA-binding polypeptides regulate transcription, usually in response to external or internal stimuli such as nutrient availability, developmental processes, and circadian rhythms. Transcription is a fundamental biosynthetic process that occurs in every eukaryotic or prokaryotic cell. During this process, an RNA polymerase enzyme uses one of the strands of a chromosomal gene as a template for the sequential assembly of ribonucleotides into ssRNA. Each resulting ssRNA molecule thereby contains a specified nucleotide sequence corresponding to the nucleotide sequence of the gene from which it was transcribed. The resulting messenger RNA (mRNA) is used as a template in the cytoplasm for the synthesis of encoded polypeptides, in the process of translation; several other ssRNA transcription products, such as transfer RNA and ribosomal RNA, are also involved in translation.

An important transcriptional regulatory function of certain dsDNA-binding polypeptides involves determining which chromosomal genes are to be transcribed. The polypeptide performs this selection process by sequence-specifically binding to dsDNA at a particular regulatory nucleotide sequence (although for some polypeptides, variations in this sequence can occur; see Beato 1989). Depending on the type of dsDNA-binding polypeptide and the particular gene involved, one or more copies of a regulatory sequence, and the polypeptide binding activity involving that sequence, can occur at a nearby transcriptional initiation site (the promoter), or at a more distant site (an enhancer) which can be located hundreds or even thousands of nucleotides away in either direction. Since transcriptional regulation of a selected gene can involve the binding of more than one class of dsDNA-binding polypeptide to the same or different regulatory nucleotide sequences, the various dsDNA-binding polypeptides can interact with each other, with other chromosomal polypeptides such as histones, and possibly with distantly-bound polypeptides.

The dsDNA-binding polypeptides are believed to bend and loop the chromosomal dsDNA within or proximal to the gene to be transcribed. This forms a pre-transcriptional polypeptide-dsDNA complex which can maintain a three-dimensional structure that is required for binding of RNA polymerase to the dsDNA, a crucial step in initiating transcription. The dsDNA-binding polypeptides thereby determine which of the two strands in the chromosomal dsDNA is to be used as the template, and the direction that the RNA polymerase should normally travel during transcription.

Since thousands of genes must be transcribed under the regulation of dsDNA-binding polypeptides (including genes which encode the dsDNA-binding polypeptides), multiple combinations of dsDNA binding interactions are continuously required. Specific interactions have therefore evolved to precisely govern the timing and extent of the coordinated cellular response to specific stimuli (Mitchell and Tjian 1988).

The sequence-specific binding to dsDNA by dsDNA-binding polypeptides also facilitates the identification and isolation of such polypeptides, for use in the synthesis of each class of PLR molecule as described herein. In one reported method, dsDNA-binding polypeptides can be isolated by first preparing a nuclear extract (using methods described in, e.g., Dignam et al 1983) from homogenized and centrifuged eukaryotic cells which should express the gene that is to be transfected by the PLR molecule. Since the selected cells express the gene of interest, the nuclear extract should contain the corresponding dsDNA-binding polypeptide.

The chromosomal gene is then isolated and molecularly cloned; or, if this has already been done, a vector which contains the gene sequence can sometimes be obtained from a public depository such as the American Type Culture Collection (Rockville, Md.) or from the scientists who first published the sequence of the gene. Radioactively labelled dsDNA restriction fragments, usually about 200 bp or less in length, are then prepared from the cloned gene, using standard methods (e.g., Sambrook et al 1989). The nuclear polypeptides and the restriction fragments are mixed together and incubated under conditions that will allow the dsDNA-binding polypeptides to bind to their corresponding dsDNA sequences; then they are processed using polyacrylamide gel electrophoresis, which separates molecules based on molecular size and charge. The binding of a dsDNA-binding polypeptide to a dsDNA restriction fragment generates a molecular complex which is substantially larger than the unbound restriction fragment; therefore, the bound polypeptide-dsDNA complex will have less electrophoretic mobility than unbound restriction fragments and will not travel as far through the gel in a given period of time. Hence, the polypeptide-dsDNA binding ("gel retardation") assay can indicate whether one or more dsDNA-binding polypeptides have bound to the specified chromosomal gene, and it also identifies the particular restriction fragment(s) that are bound by the polypeptide (Alberts et al 1989).

The radioactive polypeptide-dsDNA complexes, which are still bound together, are then eluted from the gel and digested using a nuclease, such as DNase I, which can cut dsDNA at any position. As a control, dsDNA strands which were not exposed to dsDNA-binding polypeptide are also cut by DNase I in a separate reaction. Conditions are established so that only one cut is made in most of the dsDNA molecules. As a result, dsDNA fragments having a large variety of lengths are produced by the digestion of the unbound control dsDNA; however, for the polypeptide-bound dsDNA, no cutting occurs in those sites where the dsDNA-binding polypeptides had blocked digestion by the DNase I.

The control and polypeptide-bound dsDNA reaction products are then treated to remove all polypeptides, and the dsDNA fragments from each reaction are separately applied to dsDNA sequencing gels which can distinguish between dsDNA fragments whose lengths differ by only one base pair. This size-separation step reveals, for the unbound control dsDNA, the range of degraded fragments having a large variety of lengths. By contrast, for the dsDNA which was bound by dsDNA-binding polypeptides during the DNase digestion step, there are missing fragment lengths which leave a gap or "footprint" where the dsDNA-binding polypeptides had protected the dsDNA from the DNase I. Those dsDNA fragments from the control mixture which correspond in gel position to each footprint can then be compared to a dsDNA sequencing reaction, which can be run on the same gel. This will determine the specific nucleotide sequence that is bound by each dsDNA-binding polypeptide.

The specific nucleotide sequences bound by many different specific dsDNA-binding polypeptides have been published; see, e.g., Singh et al 1989 and Windgender et al 1988.

Any such nucleotide sequence can be incorporated into chemically synthesized, radioactively labelled dsDNA probes. These probes can be used to screen phage or bacterial libraries, to identify clones which contain genes expressing the corresponding dsDNA-binding polypeptides (Singh et al 1989).

Alternately, dsDNA segments containing specific nucleotide binding sequences can be synthesized and attached to a solid support such as cyanogen bromide-activated Sepharose beads. The beads can then be poured into a glass column and used for affinity chromatography. A nuclear extract, containing nuclear polypeptides with some relatively small concentration of dsDNA-binding polypeptide, is passed through the column, using reaction conditions which promote sequence-specific binding of the dsDNA-binding polypeptides in the nuclear extract to the immobilized dsDNA probes (Briggs et al 1986). Those dsDNA-binding polypeptides which bind to the specific nucleotide sequence of dsDNA immobilized on the beads remain in the column, while the other nuclear polypeptides (including dsDNA-binding polypeptides with different binding specificities) pass through the column. Subsequently, the reaction conditions are changed to release the bound dsDNA-binding polypeptides from the immobilized dsDNA. The released polypeptides are then washed out of the column and concentrated in purified form. This process can generate a quantity of polypeptide sufficient for amino acid sequencing. The amino acid sequence data will allow the chemical synthesis of ssDNA probes for the isolation and cloning of the gene which encodes the specified dsDNA-binding polypeptide (Landschulz et al 1988).

The methods outlined above can be used to isolate a gene that expresses a dsDNA-binding polypeptide from many types of cells, including human cells from many particular types of tissues or individual cells such as lymphocytes. The isolated gene can be incorporated into bacterial, insect, or other expression vectors to facilitate the production and purification of the dsDNA-binding polypeptide in large quantities (Smith and Johnson 1988). This allows the polypeptide to be tested for its ability to enter nuclei, by using any of several techniques. For example, fluorescent or other labelling molecules can be attached to a dsDNA-binding polypeptide, and the labelled polypeptide can then be inserted into cell cytoplasm using techniques such as microinjection or electroporation. The cells can then be assayed by techniques such as microfluorophotography to determine the presence of the fluorescent polypeptide inside the nuclei (Peters 1986). The isolated dsDNA-binding polypeptides can also be tested by using the gel retardation and footprinting techniques described above.

The techniques summarized above are being used by numerous research teams to identify and isolate dsDNA-binding polypeptides. Table 1 contains a sample of such polypeptides with published sequence data; numerous other dsDNA-binding polypeptides have been isolated and sequenced, and their sequence data are listed in Genbank, a computerized database run jointly by the National Institutes of Health (Bethesda, Md.) and Intelligenetics (Mountain View, Calif.), and in other computerized databases such as the databases run by European and Japanese molecular biology organizations. The nucleotide sequence of a dsDNA-binding polypeptide can also allow the chemical synthesis of specific ssDNA primers for use in the polymerase chain reaction (PCR). This can amplify the gene which encodes the dsDNA-binding polypeptide for subsequent molecular cloning into an expression vector for polypeptide synthesis and purification. Any dsDNA-binding polypeptide which has been (or which is in the future) cloned, sequenced, or isolated can be tested as described herein to determine whether it is suitable for use as a polypeptide component in a PLR molecule as described herein.

The term "dsDNA-binding polypeptide" is used herein to include proteins or portions thereof which can carry out the functions of nuclear transport and sequence-specific binding to dsDNA. It also includes dsDNA-binding polypeptides which are associated with RNA; such protein-RNA complexes are usually called ribonucleoproteins (RNP's). A naturally-occurring occurring RNP has been shown to site-specifically bind to chromosomal dsDNA (Davis et al 1989). It also includes polypeptides which may have additional characteristics other than dsDNA binding; e.g., Santoro et al 1991 describes polypeptides which sequence-specifically bind to both dsDNA and ssDNA. It also includes polypeptides which sequence-specifically bind only to ssDNA (Wilkison et al 1990). It also includes polypeptides in which one or more amino acids have been genetically altered from their natural form, such as by substitution, deletion, addition, or rearrangement (e.g., Zuckermann and Schultz 1988 and O'Neil et al 1990) or by chemical, enzymatic, electromagnetic radiation, pressure treatment, or other alteration of one or more amino acid residues (see, e.g., Lyu et al 1991, Towler et al 1988, Suslick 1990, and Gilmour and Lis 1985). It also includes chimeric (hybrid) polypeptides; for example, a genetically engineered gene can be synthesized and expressed in host cells to produce a selected nuclear localization sequence (NLS) from one naturally-occurring dsDNA-binding polypeptide combined with a dsDNA-binding domain from a different dsDNA-binding polypeptide (see Beato 1989). This domain interchange can increase the versatility of polypeptides used as described herein as the polypeptide component.

It is also believed that polypeptides which indirectly bind to dsDNA in a site-specific manner can be used as described herein, provided that they can migrate into the nucleus and bind to sequence-specific dsDNA-binding polypeptides. A number of indirect-binding polypeptides exist in nature, such as the herpes simplex virus and adenovirus nuclear polypeptides VP16 and E1A, respectively (Ptashne and Gann et al 1990). The indirect-binding approach can also use chimeric proteins comprising a nuclear localization sequence coupled to a portion of an antibody which binds to a known dsDNA-binding protein.

Polypeptides which perform the functions necessary to carry out this invention can be isolated from various natural sources. For example, Baim et al 1991 discuss chimeric polypeptides comprising prokaryotic and eukaryotic portions. The chimeric polypeptides bound in a sequence-specific manner to prokaryotic dsDNA that had been transfected into eukaryotic cells. Although prokaryotic transcription-regulating polypeptides normally will not contain a nuclear localization sequence (NLS), the chimera was produced by molecularly cloning the prokaryotic sequence with nucleotide sequences coding for a eukaryotic NLS, and for a eukaryotic transcriptional regulatory domain. The prokaryotic portion of the chimeric polypeptide could govern transcription of the recombinant eukaryotic gene by changing the conformation of the chimeric polypeptide in a manner which responded either to a chemical inducer added to the transfected cells, or to the temperature at which the cells were cultured. Similar or analogous chimeric polypeptides can be tested in vitro or in vivo to determine whether they can sequence-specifically bind to eukaryotic genes, regulate transcription, and enable homologous recombination when incorporated into a PLR molecule as described herein.

In order to avoid a potential immunogenic reaction, the use of dsDNA-binding polypeptides as components of PLR molecules should be limited to in vitro transfection procedures, or the polypeptides should be isolated from an immunologically similar host. In most situations involving in vitro transfection, the transfected cells can be placed into the body of a human patient or other eukaryote by means such as injection, without provoking an immunogenic reaction. Microacceleration of nucleic acid directly into organs in vitro or in vivo suggests another means of avoiding an immunogenic reaction (see Zelenin et al 1991). This technique, as well as in situ electroporation using electrodes implanted into organs, might be useful for transfecting cells and organs in vivo using PLR molecules. As used in the claims, the culturing of transfected cells can include in vivo or in situ culturing of transfected organs inside an intact animal.

The Linker (L) Component: A Chemical Crosslinking Reagent

The linker component 20 is a chemical crosslinking reagent which enables the covalent coupling of the polypeptide component 10 to the rDNA component 30. The distinction made herein between covalent and non-covalent bonds follows conventional usage (e.g., Vollhardt 1987). Highly specific methods (such as the method which uses $BS^3$, discussed below) are preferable since they will produce fewer undesired byproducts; however, less specific chemicals reagents (such as glutaraldehyde, also discussed below) can be used if desired, provided that steps are taken to purify PLR molecules 50 having the desired structure while removing undesired conjugates and aggregates.

In one preferred embodiment, the linker component 20 is bis(sulfosuccinimidyl)suberate (abbreviated as $BS^3$). This reagent 20, shown in FIG. 1, contains two N-sulfosuccinimide(NHS)ester groups 22 and 24, each of which can react covalently and with high specificity with primary amino groups on other molecules. The two NHS ester groups 22 and 24 are separated by an alkane spacer arm 26 which is six carbon atoms in length, which reduces steric hindrance and improves the efficiency of crosslinking. The presence of two reactive groups defines the $BS^3$ reagent 20 as a bifunctional crosslinker, and since both of the reactive groups are identical, $BS^3$ is defined as a homobifunctional crosslinker. The $BS^3$ reagent is water-soluble, and at physiological pH it reacts covalently, stably, and efficiently with primary amino groups (Anjaneyulu and Staros 1987), which includes the primary amino nitrogen atom 13 on the dsDNA-binding polypeptide 10 and the primary amino nitrogen atom 37 on the rDNA component 30 (shown in FIG. 1) when those components are assembled into a PLR molecule 50, as described below. The sodium salt of $BS^3$ is available from companies such as Pierce Chemical Co. (Rockford, Ill.).

Other chemical crosslinkers can contain two reactive groups with different crosslinking specificities, hence, they are defined as being heterobifunctional. For example, the crosslinker succinimidyl 4-(N-maleimidomethyl) cyclohexane-1-carboxylate (abbreviated as SMCC) can be reacted sequentially with a mercapto group on one molecule, and then with a primary amino group on another molecule, to form a covalently-bonded conjugate (Partis et al 1983).

An alternate approach is suggested by a different covalent chemical crosslinker, N-succinimidyl 3-(2-pyridyldithio)-propionate (abbreviated as SPDP). This reagent can be directly reacted with primary amino groups in ssDNA (Fallon and Malcom 1983), which eliminates the need to add a primary amino group to an ssDNA segment for a subsequent reaction with a crosslinker. However, the direct reaction of SPDP with ssDNA cannot be easily controlled to cause it to react with a specific desired base. Also, the SPDP reagent subsequently forms conjugates that contain a disulfide bond, which is not preferred for use as described herein, since they tend to be cleaved inside the cell. However, it may be possible to use crosslinking reagents such as $BS^3$ which do not form disulfide bonds and which can be directly incorporated at specified locations into DNA during its chemical synthesis. The ssDNA-crosslinker could then be hybridized to complementary ssDNA to form a dsDNA-crosslinker conjugate for subsequent use as described herein.

Various other crosslinking reagents can also be used to covalently couple DNA segments to polypeptides, with varying degrees of efficiency. For example, glutaraldehyde contains two aldehyde (—CHO) groups, each of which can react with a number of different substrates (Renz 1983). Although glutaraldehyde crosslinking will generate higher levels of unwanted by-products than the $BS^3$ crosslinking reagent discussed above, glutaraldehyde and other similarly non-specific chemical reagents can be used, provided that steps are taken to purify the desired PLR molecules and remove any undesired by-products. Similar considerations also apply to other covalent crosslinking methods which have less specificity than $BS^3$. This can include electromagnetic radiation used at wavelengths which do not damage nucleic acid. For example, selected wavelengths of ultraviolet light can be used either alone or with psoralens, which are UV-sensitive photochemical reagents (Oser et al 1990; Gilmour and Lis, 1985).

It is also possible to couple polypeptides to DNA segments by using the non-covalent but high binding affinity between a ligand such as biotin and a polypeptide such as avidin or streptavidin (Bayer et al 1990; Green 1975). For example, biotin-modified nucleoside triphosphates can be incorporated into dsDNA, while streptavidin is chemically coupled to another polypeptide such as a dsDNA-binding polypeptide. When these two molecules are mixed, the biotin-streptavidin binding reaction will couple a biotin-DNA conjugate to a streptavidin-polypeptide conjugate.

Alternately, an enzymatic method can be used in a process which covalently couples a polypeptide molecule to a DNA molecule. For example, an enzyme known as gamma-transglutaminase can couple primary amino groups from different molecules to each other (Parameswaran et al 1990). This enzyme could couple a DNA molecule which has been modified to contain an accessible primary amino group (using a technique such as described herein) to a primary amino group on a polypeptide.

Crosslinking can also be facilitated by incorporating one or more ribonucleotides into the 3'-terminus of the rDNA by using the enzyme T4 RNA ligase. The ribonucleotide can be reacted with sodium metaperiodate, sodium cyanoborohydride, and the epsilon primary amino group of L-lysine to convert the ribose group to N-morpholine, which covalently crosslinks the ribonucleotide to the L-lysine (LeMaitre et al 1987). This method could also be used to crosslink the polypeptide component to DNA, thereby completing assembly of a PLR molecule.

The Recombinant (R) Component

The recombinant (R) component comprises a DNA segment having a specified nucleotide sequence and a reactive group which enables the DNA segment to be crosslinked to a DNA-binding polypeptide. In a preferred embodiment depicted in FIG. 1, the R component 30 comprises a dsDNA molecule 32 coupled to a primary amino nitrogen atom 37. The primary amino nitrogen atom 37 is a reactive part of a primary amino group. A primary amino group is incorporated into a synthetic chemically-altered structure referred to herein as a primary amino modifier 34.

In one mode of synthesis, a selected dsDNA segment 32 can be isolated or assembled and molecularly cloned using well-known procedures (e.g., Sambrook et al 1989). The specified dsDNA segment 32 is removed from the cloning vector nucleotide sequences 33 and from any other undesired eukaryotic sequences 31 which flank desired dsDNA segment 32, by using two restriction endonuclease enzymes. The two enzymes have different nucleotide recognition sequences, such as the sequences 35 and 36 shown in FIG. 2.

To facilitate enzymatic incorporation of a reactive group (such as primary amino modifier 34) into the R component 30, one of the restriction endonucleases should generate a 5'-terminus having a single unpaired adenosine nucleotide, such as the sequence GATC, which is generated by the restriction endonuclease BamHI at cleavage site 35. Other examples of restriction endonucleases which generate 5'-termini containing a single adenosine nucleotide include BclI, BglII, and NcoI. The reference to a "5'-terminus" indicates that the unpaired nucleotides are at the 5' end of a strand of dsDNA. This allows enzymatic incorporation of additional nucleotides at the 3' end of the complementary strand of dsDNA.

Figure 2:
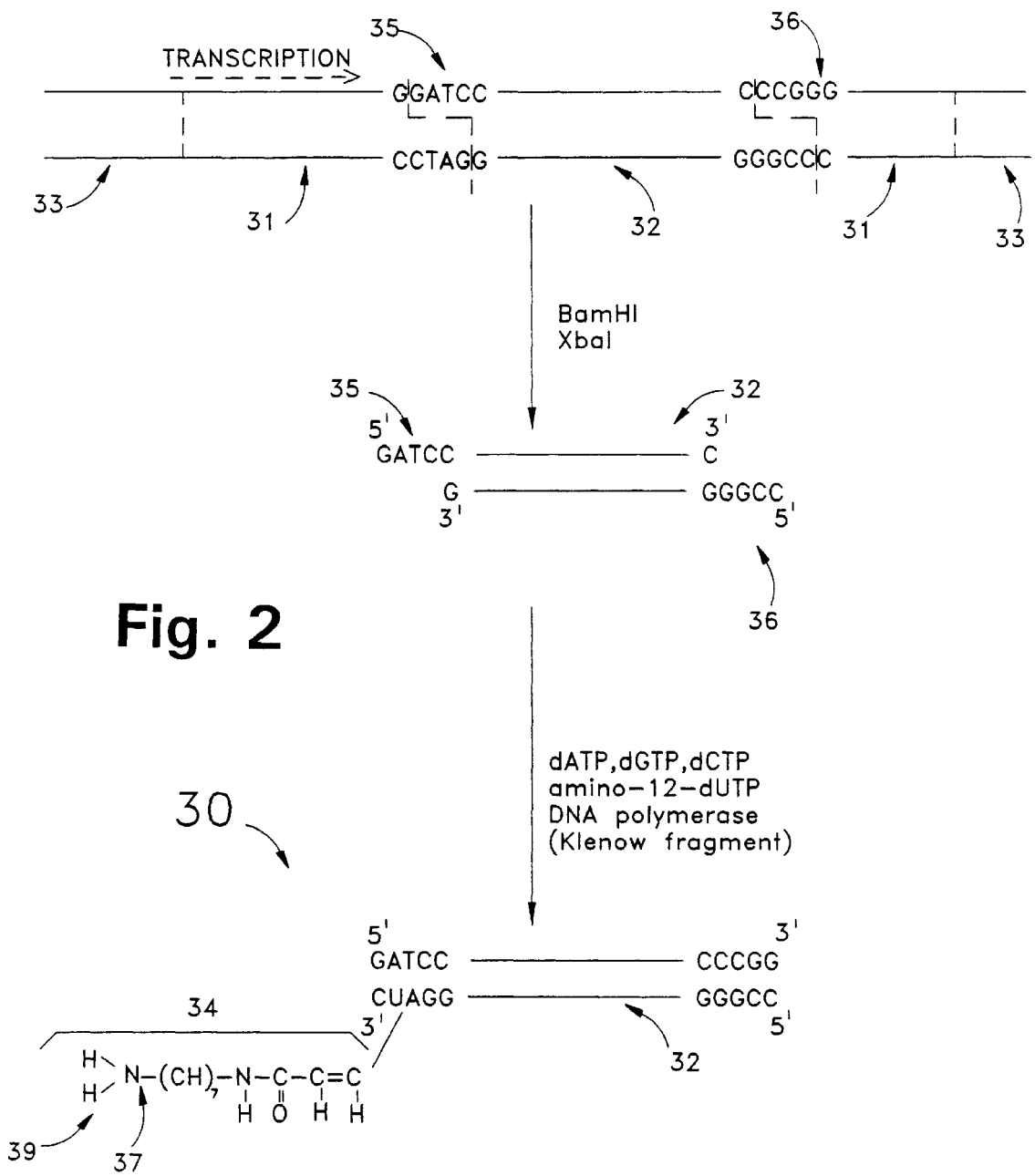
FIG. 2 depicts the synthesis of a recombinant DNA component containing an incorporated modifier which provides an accessible primary amino nitrogen atom for crosslinking purposes.

The 5' terminus created by the other restriction endonuclease (indicated as terminus 36 in FIG. 2) should not contain any unpaired adenosine nucleotides; a suitable example is the sequence CCGG, which is generated by the restriction endonuclease XmaI as shown in FIG. 2. Other restriction endonucleases which generate 5' termini having no unpaired adenosine nucleotides include EaeI, EagI, and KasI. Alternately, a restriction endonuclease can be used which generates a "blunt end" having no unpaired nucleotides. However, this would prevent the use of certain other techniques discussed below, such as the incorporation of nucleotide analogs into terminus 36, which can give the modified dsDNA segment additional or enhanced features such as greater intracellular stability.

To properly orient the primary amino modifier 34 with respect to the specified dsDNA segment 32, the 5'-terminus containing the single unpaired adenosine nucleotide should be located closest to the gene's origin of transcription, which is shown proceeding in the direction indicated by the arrow near the top of FIG. 2.

Following digestion by both restriction endonucleases, the desired dsDNA segment 32 can be separated from other dsDNA fragments such as 31 and 33 by means such as agarose gel electrophoresis. Fragment 32 can be eluted from the gel, purified, and reacted to allow the enzymatic incorporation of a primary amino modifier 34 into one strand of the dsDNA segment 32. An example reagent which can be used to incorporate a primary amino modifier into a segment of dsDNA comprises 5-amino(12)-2'-deoxyuridine-5'-triphosphate, abbreviated as amino-12-dUTP. This reagent is a synthetic, chemically-altered dUTP nucleotide which has a primary amino group attached to position 5 of the uracil base. The primary amino group is at the end of a flexible chain 12 atoms in length, which increases its accessibility for the subsequent crosslinking reaction.

The amino-12-dUTP reagent is included in a reaction mixture which includes (a) the purified dsDNA molecule 32; (b) the amino-12-dUTP reagent; (c) three other nucleoside triphosphates (dATP, dGTP, and dCTP) which are used to synthesize dsDNA; and (d) a dsDNA polymerase enzyme such as dsDNA polymerase I (Klenow fragment). The dsDNA polymerase uses the triphosphate reagents to extend the 3' ends of the two dsDNA strands, using nucleotides that are complementary to the unpaired 5' nucleotides produced by both restriction endonucleases. During this reaction, the amino-12-dUTP molecule is enzymatically incorporated into the dsDNA opposite any adenosine nucleotides. Since only one adenosine nucleotide was located in the 5'-terminus generated at site 35, and since no adenosine nucleotides were present at the 5'-terminus 36, only one amino-12-dUTP residue 34 is added to the dsDNA molecule 32. This residue 34 includes a spacer chain which terminates in the primary amino group comprising the nitrogen atom 37.

Various other reagents can be used in a similar manner. For example, a primary amino group chemically attached to dATP (rather than dUTP) can be synthesized or may be commercially available. The primary amino group is attached to the adenosine base at position 8 by a chain which is seven atoms in length. This amino-8-dATP reagent could be used to enzymatically incorporate a reactive nitrogen atom in a 5'-terminus having an unpaired thymidine nucleotide. A primary amino group included within a 12-atom flexible chain can also be incorporated into ssDNA by chemical synthesis, using known techniques. This ssDNA strand with a primary amino group can then be hybridized with a complementary ssDNA in the normal manner.

Construction of the PLR Molecule

As shown in FIG. 1, the crosslinker molecule 20 ($BS^3$ in the embodiment discussed herein) is first coupled to the R component 30 (i.e., the rDNA component 30) in a reaction designated as Reaction A in FIG. 1, which forms linker-rDNA conjugate 40. This conjugate 40 is subsequently reacted with the dsDNA-binding polypeptide 10, in Reaction B.

In a reaction between $BS^3$ and a polypeptide, $BS^3$ can react stably and efficiently with N-terminal amino acids and specifically with the side chain of a lysine residue. The side chain of a lysine residue extends four carbon atoms in length and terminates in a primary amino group, which is often called an epsilon amino group. The reaction of $BS^3$ with the epsilon amino group of a lysine residue on the surface of a polypeptide is favored because lysine is hydrophilic and is therefore frequently located on accessible exterior surfaces of polypeptides; the four-carbon side chain that terminates in the epsilon amino group further enhances the accessibility of these groups.

The $BS^3$ can be used as a crosslinking agent to couple the rDNA 30 to dsDNA-binding polypeptide 10. However, there are two important considerations: (1) a polypeptide molecule may have more than one accessible amino group on its surface, and (2) different types of polypeptides may have substantially different numbers of accessible amino groups. To simplify the crosslinking reaction and minimize the need for different reaction conditions for different types of polypeptides, and to avoid undesired reactions such as the formation of polypeptide-polypeptide dimers or the crosslinking of more than one $BS^3$ molecule to a single polypeptide molecule, $BS^3$ preferably should be reacted first with the rDNA molecule 30. In this reaction, shown as Reaction A in FIG. 1, the primary amino modifier 34, which was incorporated into the rDNA 30, is shown reacting with the carbonyl carbon atom 23 in the N-sulfosuccinimide ester group 22 of the $BS^3$ reagent 20. Reaction A covalently bonds the primary amino nitrogen atom 37 of the rDNA 30 to the carbonyl carbon atom 23, resulting in a stable amide bond 28. During this reaction, a hydrogen atom 39 bound to the primary amino nitrogen atom 37 bonds to oxygen atom 27, with the release of the byproduct, N-hydroxysulfo-succinimide 22A.

Reaction A should be performed using both the $BS^3$ reagent 20 and the rDNA 30 at suitable concentrations, approximately in the nanomolar or micromolar range, and with a substantial or large molar excess of $BS^3$ (such as about 10:1 or greater molar ratio). The molar excess of $BS^3$ inhibits the formation of dimers containing two rDNA molecules coupled to a single $BS^3$ residue. Also, since rDNA molecules are outnumbered during Reaction A, any $BS^3$ molecule 20 which reacts with an rDNA molecule 30 will normally retain an unreacted N-sulfosuccinimide ester group 24 throughout the remainder of Reaction A. The reactive group will therefore remain free for a subsequent reaction with a dsDNA-binding polypeptide 10 during Reaction B.

If any $BS^3$ molecules react with two rDNA molecules during Reaction A, the resulting dimers would not be able to react subsequently with a dsDNA-binding polypeptide, since both of the reactive groups of the $BS^3$ reagent will be consumed. The undesired dimers can be removed from the mixture during purification. For example, upon completion of Reaction A, the desired linker-rDNA component 40 can be identified using polyacrylamide gel electrophoresis and purified and concentrated by means such as gel chromatography and vacuum dialysis, using standard techniques (e.g., Jablonski et al 1986). Storage of the linker-rDNA component 40 below 0° C. would prolong stability and facilitate commercial shipping.

In Reaction B, the linker-rDNA component 40 is coupled with the dsDNA-binding polypeptide 10. In this reaction, shown in the lower half of FIG. 1, an epsilon amino nitrogen atom 13 of the dsDNA-binding polypeptide 10 covalently bonds with the carbonyl carbon atom 25 of the N-sulfosuccinimide ester group 24, resulting in a stable amide bond 17. Also during this reaction, a hydrogen atom 15 bound to the epsilon amino nitrogen atom 13 on the dsDNA-binding polypeptide 10 bonds to oxygen atom 29, with the resulting release of another molecule of N-hydroxysulfo-succinimide 24A.

The completed conjugate which results from Reactions A and B is the PLR molecule 50, which contains a linkage 42 that is twenty atoms long, between the uracil base in the dsDNA molecule 32 and the now-secondary amino nitrogen atom 13 on the dsDNA-binding polypeptide.

In general, the final crosslinking reaction should be performed by mixing the linker-rDNA conjugate 40 and the dsDNA-binding polypeptide 10 at approximately nanomolar or micromolar concentrations. Preferably, a molar excess of the polypeptide 10 should be used, to minimize the formation of aggregates having multiple rDNA molecules coupled to a single polypeptide. Analysis and purification of the completed PLR molecule 50 can be performed by methods such as gel chromatography (Bowerman et al 1989).

Since Reactions A and B use an identical mechanism, similar conditions should be suitable for both reactions in most cases. In general, buffers such as citrate or borate which contain no competing amine or mercapto groups, or any phosphate groups which might precipitate $BS^3$, should be used (Staros et al 1987). If desired, the polypeptide component can be bound to its specific nucleotide binding sequence before crosslinking. This can protect the nucleic acid binding domain of the polypeptide from being inactivated during the crosslinking process. Although the details of any specific reaction will depend on factors such as the exact characteristics of the dsDNA-binding polypeptide and the buffer, reactions in neutral or sufficiently basic conditions (such as about pH 7 to about pH 9) at room temperature ranges (approximately 22° C.) should provide adequate reactivity for the primary amino nitrogen atoms 13 and 27 without jeopardizing the stability of the N-sulfosuccinimidyl ester groups 22 and 24 (Anjaneyulu and Staros 1987). The rate and extent of both reactions can be determined by methods such as spectrophotometry, using increased optical density at 260 nm due to the production of N-hydroxysulfosuccinimide byproducts 22A and 24A. Gel electrophoresis or gel chromatography can also be used to determine the rate and extent of both reactions (e.g., Jablonski et al 1986).

Use of the PLR Molecule in Transfection

The PLR molecule 50 can be transfected into the cytoplasm of eukaryotic cells by using one of the methods discussed in the Background section, such as microinjection or electroporation. One particular method of electroporation, often referred to as "Baekonization" (discussed in the Background section), has been shown to be capable of transferring polypeptides and DNA simultaneously into the same cell; accordingly, it should be well-suited for use in the subject invention. It can be used with relatively high cell densities (more than $10^5$ eukaryotic cells per milliliter), and cell viability usually remains high.

Figure 3:
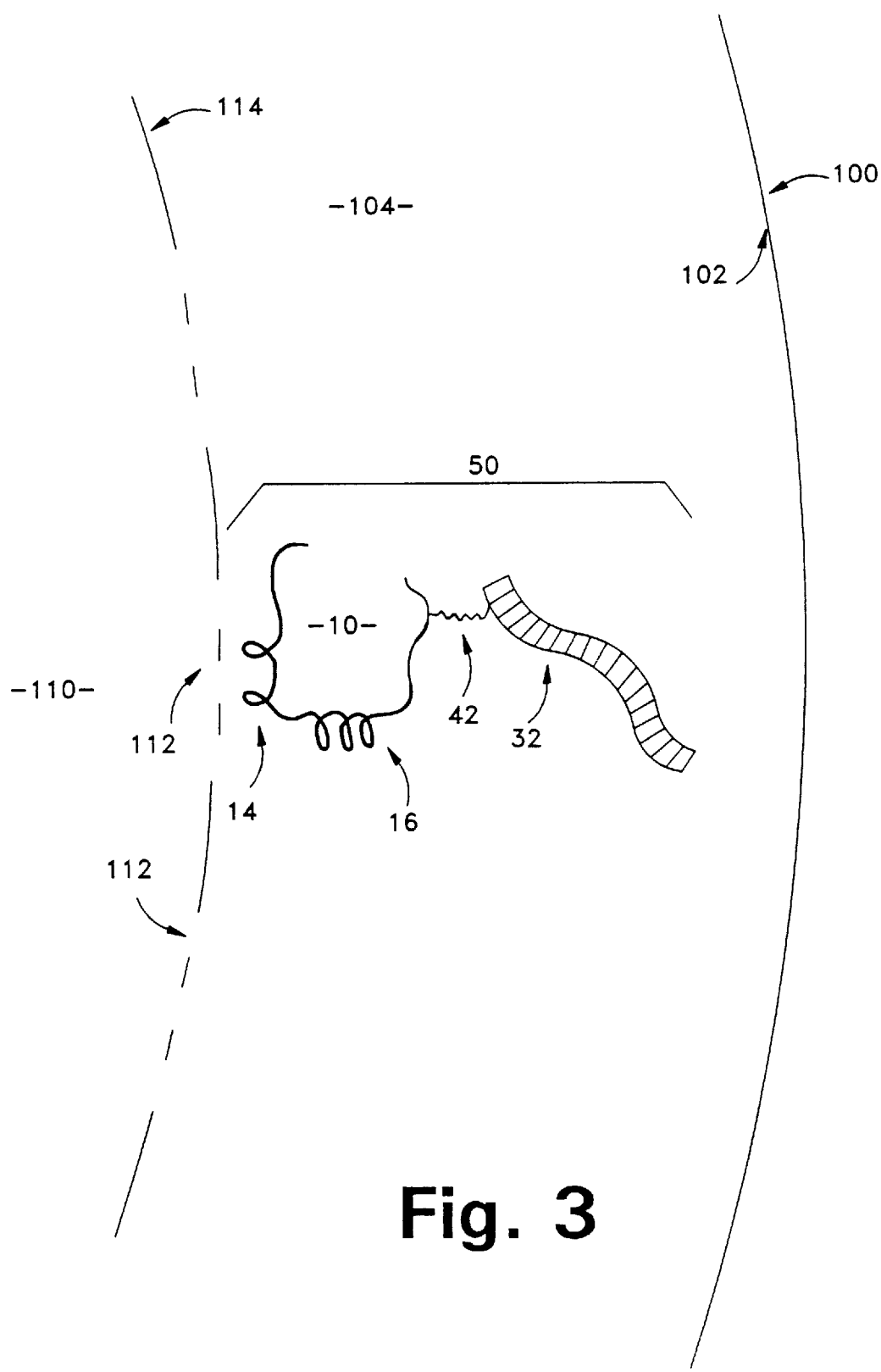
FIG. 3 depicts the polypeptide component of a PLR molecule during intracellular transport through the cytoplasm and into the nucleus.

Referring to FIG. 3, the PLR molecule 50 is depicted within a eukaryotic cell 100, following its transfer through the outer cell membrane 102. The PLR molecule 50 is located in the cellular cytoplasm, shown generally at 104, from which it must migrate into the nucleus 110 by means of a nuclear pore 112 located in the nuclear membrane 114.

In order to perform these functions, the PLR molecule 50 must maintain its structural stability in each of the above cellular compartments. The use of a dsDNA-binding polypeptide as the polypeptide component 10 of a PLR molecule 50 takes advantage of the fact that dsDNA-binding polypeptides are synthesized naturally in the cytoplasm of cells, and have evolved sufficient resistance to cytoplasmic polypeptide-degrading enzymes (proteases) to survive migration through the cytoplasm and into the nucleus, to fulfill their natural functional roles (Arfin and Bradshaw 1988).

Such dsDNA-binding polypeptides have also evolved the ability to avoid entering lysosomes, which are acidic organelles in the cytoplasm containing proteases and DNA-degrading enzymes (DNases). In contrast, when other methods of transfection are used which involve introducing segments of DNA into the cytoplasm (by means such as electroporation, enclosing the DNA within liposomes, or crosslinking the DNA to polypeptides which bind to cellular membrane receptors which are subsequently internalized by the cell), it is found that most of the DNA and other macromolecules which enter a cell are transported to the lysosomes (Cheng et al 1983; Mannino and Gould-Fogerty 1988). Once inside the lysosomes, the macromolecules can be entirely degraded or damaged, the latter of which can promote subsequent mutations in the DNA by cytoplasmic and nuclear enzymes. This can cause a low transfection frequency and the production of unwanted genotypes (Chiang and Wilson 1987). Therefore, the natural cytoplasmic survival characteristics of dsDNA-binding polypeptides which normally are transported into the nucleus are utilized when such polypeptides are incorporated into a PLR molecule 50.

The use of $BS^3$ as the crosslinking reagent also contributes to the stability of the PLR molecule 50, since the crosslinking reactions produce amide bonds 17 and 38, which are sufficiently stable in the reducing environment of the cytoplasm. In contrast, disulfide bonds (—S—S—) such as used by Cheng et al 1983 to crosslink alpha-2-macroglobulin to dsDNA, would be reduced to unlinked mercapto groups (—SH HS—). This could occur in the acidic lysosomes (pH 5); additionally, if any macromolecules avoid lysosomal degradation, they would nevertheless tend to be unlinked in the cytoplasm 104 by the tripeptide, glutathione, and by the polypeptide thioredoxin (Mahler and Cordes 1971). Therefore, by using $BS^3$ as the crosslinking reagent, both crosslinkages are more likely to remain intact, increasing the ability of the PLR molecule 50 to carry out its functional role in transfection.

The use of double-stranded DNA in component 30 in the PLR molecule 50 can also contribute to the intracellular stability of the PLR molecule. Various items of prior art have used single-stranded DNA in transfection (e.g., Cheng et al 1983), despite ssDNA being more susceptible to degradation by DNase enzymes (Lewin 1990). However, ssDNA has been used without crosslinking to a polypeptide for site-specific transfection (Rauth et al 1986). To improve the efficiency of ssDNA transfection, the rDNA component 30 can also comprise ssDNA crosslinked to the polypeptide component 10. This can be done by constructing the rDNA component as described above, and then separating (denaturing) the two DNA strands by increasing the reaction temperature and decreasing the salt concentration. The ssDNA strand comprising the amino-12-dUTP can be separated from the other ssDNA strand by means such as agarose gel electrophoresis, before crosslinking to the polypeptide component as described above.

To further increase the resistance of ssDNA or dsDNA in the rDNA component 30 to cytoplasmic degradation, nucleotide analogs which normally are not contained in DNA, such as 2'-deoxy-nucleoside-5'-(alphathio)triphosphates, 3'-deoxynucleoside-5'-triphosphates, and 2',3'-dideoxynucleoside5'-triphosphates (sold by suppliers such as Pharmacia Inc., Piscataway, N.J.) can also be incorporated into one or both of the 5'-termini of the dsDNA segment 32 (Chiang and Wilson 1987). If desired, this can be done during the same enzymatic reaction that is used to incorporate the amino-12-dUTP molecule into the dsDNA segment 32, described above and shown in FIG. 2.

The rDNA can also contain other non-natural structures such as chemically synthesized carbocyclic nucleotides. These can be enzymatically incorporated by terminal transferase to increase resistance of the rDNA to cellular nucleases, and still allow nucleic acid hybridization (Sagi et al 1990).

Additionally or alternatively, the enzyme alkaline phosphatase can be used to convert 5'-terminal phosphate groups (—$OPO_3H_2$) to hydroxy (—OH) groups, to prevent unwanted enzyme-driven polymerization of the rDNA component 30 inside the nucleus.

As mentioned above, the stability of a PLR molecule 50 inside a cell cytoplasm 104 is promoted by reducing the amount of time that the PLR molecule remains in the cytoplasm. In other transfection methods, DNA tends to randomly migrate around and through the cytoplasmic cytoskeleton, while undergoing progressive degradation and mutation until a small percentage can enter the nucleus 110 by passive diffusion or other unknown mechanisms. By contrast, when a dsDNA-binding polypeptide is used as a component of a PLR molecule 50, this allows the PLR molecule 50 to take advantage of a "nuclear localization signal" (NLS), which is depicted by polypeptide region 14 in FIGS. 1 and 3.

NLS domains are amino acid sequences which have evolved in polypeptides thereby facilitating migration of a polypeptide from the cytoplasm into the nucleus. In one set of experiments, specified nuclear polypeptides containing NLS domains enabled the transport of a polypeptide-RNA complex into the nucleus (Mattaj and DeRobertis 1985). In another set of experiments, a single NLS was shown to transport into the nucleus a colloidal gold particle (with a mass greater than 360 bp of dsDNA), which otherwise could not enter the nucleus (Feldherr and Dworetzky 1988). NLS domains are further discussed in various publications such as Alberts et al 1989.

The NLS domain 14 of the dsDNA-binding polypeptide 10 which is incorporated into a PLR molecule 50 can thus significantly reduce the amount of time that the PLR molecule spends in the cytoplasm 104 of a transfected cell, by facilitating binding and penetration into the nucleus 110.

After entering the nucleus 110, a PLR molecule 50 can facilitate site-specific genetic recombination. This is accomplished when the dsDNA-binding component 10 of the PLR molecule 50 contacts a chromosome 120 and then moves along one or more chromosomes 120 until it locates and binds to the specific nucleotide sequence 122 where the polypeptide naturally binds. The binding site can be located proximally to a selected chromosomal gene; as used herein, proximal location includes sequences that become positioned adjacent to a region of homology due to polypeptide-induced looping of the chromosomes. This gene will contain a nucleotide sequence that is sufficiently homologous to the rDNA component 30 of the PLR molecule 50, thereby facilitating homologous recombination as discussed below.

By contrast, when other methods of transfection (such as retroviruses) are used which do not couple a dsDNA molecule to a dsDNA-binding polypeptide, site-specific recombination of the dsDNA segment with a homologous chromosomal sequence is very rare. This occurs since the dsDNA segments randomly diffuse within the nucleus, where they are exposed to nuclear DNases which actively degrade dsDNA segments. The resulting degradation, mutation, and increased possibility of unwanted integration at nonhomologous sites can disrupt the functioning of other necessary genes (Chiang and Wilson 1987). In addition, the randomness of the diffusion process also explains why dsDNA segments by themselves are unlikely to locate a site for homologous genetic recombination, since the human genome contains approximately 3 billion base pairs (Lewin 1990).

Accordingly, a PLR molecule 50 as described herein utilizes its dsDNA-binding polypeptide component 10 as it efficiently scans large areas of the genome. Upon reaching a gene 124 that can be regulated in part by the specified dsDNA-binding polypeptide 10, the polypeptide uses its dsDNA-binding domain 16, which has evolved so as to specifically enable non-covalent, yet stable, sequence-specific binding to the nucleotide binding sequence 122 (Johnson and McKnight 1989).

A particular nucleotide binding sequence which is bound by one or more dsDNA-binding polypeptides may occur in more than one chromosomal gene. For example, a single dsDNA-binding polypeptide can bind to the nucleotide binding sequences of both an alpha globin gene and a beta globin gene. Accordingly, the possibility exists that chromosomal binding may position a PLR molecule adjacent to a chromosomal gene which is not homologous to the rDNA component of the PLR molecule. If this occurs, non-homologous recombination might possibly occur, but this would be rare, and the PLR molecule would eventually disengage from the nucleotide binding sequence.

A recognized nucleotide binding sequence 122 should not be contained within the dsDNA 32 of the PLR molecule 50. This could prevent the dsDNA-binding polypeptide 10 of the PLR molecule 50 from binding to the dsDNA 32 of the same or other PLR molecules, which could reduce the transfection frequency.

In the preferred embodiment, the dsDNA 32 of a PLR molecule 50 also should not contain any recognized nucleotide binding sequences from any other genes, so that other naturally occurring dsDNA-binding polypeptides cannot bind to the rDNA 30 of the PLR molecule 50. In this way, the dsDNA 32 of the rDNA component 30 is also unlikely to interfere with the normal cellular functions of other dsDNA-binding polypeptides (Rabek et al 1990).

Since the structure of the PLR molecule 50 facilitates its efficient transport as it scans for its specified nucleotide binding sequence, this can also reduce the likelihood of unwanted integration events which might otherwise occur between the dsDNA 32 and genomic regions of partial homology (Chiang and Wilson 1987).

Figure 4:
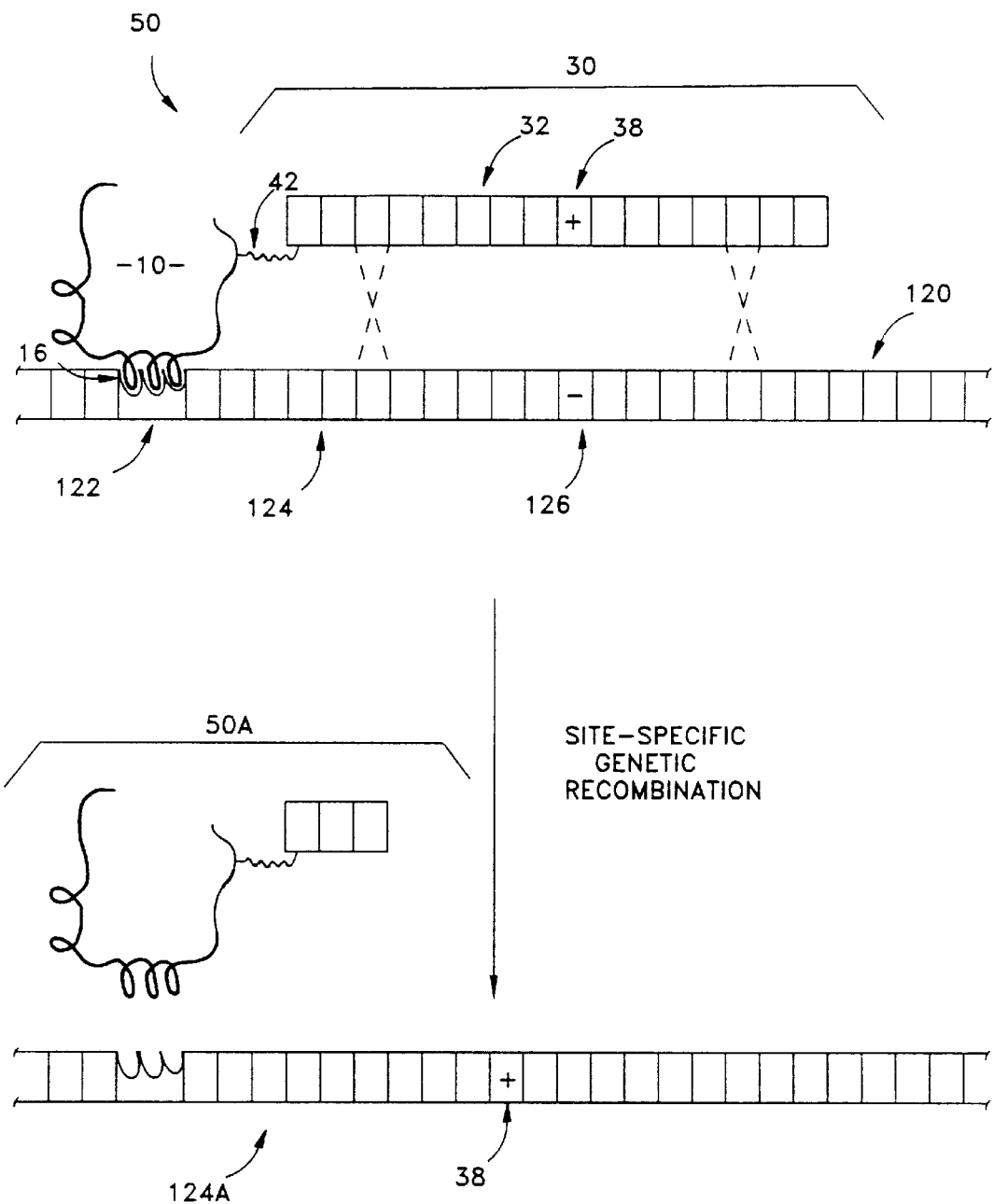
FIG. 4 depicts the polypeptide component of a PLR molecule bound to chromosomal dsDNA, so that the recombinant dsDNA component of the PLR molecule is positioned near homologous chromosomal dsDNA. Also depicted, by dotted crosses, are sites of homologous recombination, a process which causes a defective portion of a chromosomal gene to be replaced by a properly coding portion of a recombinant dsDNA component of the PLR molecule, to generate a normal gene which encodes a properly functioning polypeptide.

Referring to FIG. 4, the PLR molecule 50 is shown with its dsDNA-binding domain 16 bound to the specific nucleotide recognition sequence 122. This binding reaction positions the dsDNA 32 of the rDNA component 30 within or proximal to a chromosomal gene 124 having a nucleotide sequence which is sufficiently homologous to that of the dsDNA 32. This can facilitate the genetic process of homologous recombination. During this process, a portion of the nucleotide sequence of the dsDNA 32 of the rDNA component 30 replaces a portion of the homologous chromosomal nucleotide sequence 122.

To further facilitate this type of genetic recombination, the rDNA component 30 should contain linear dsDNA, preferably about 200 bp or more in length (Rubnitz and Subramani 1984; Deng and Capecchi 1992). To facilitate homologous recombination, the rDNA component 30 should also have maximal nucleotide sequence homology with the chromosomal nucleotide sequence 124, consistent with the necessity of recombining a normal nucleotide sequence into the defective chromosomal gene for purposes such as gene therapy.

For example, FIG. 4 depicts the replacement of a chromosomal gene 124 containing a defective nucleotide sequence 126; i.e., the chromosomal gene has a nucleotide sequence which encodes a defective polypeptide which does not function properly, as occurs in genetic diseases such as sickle cell anemia or cystic fibrosis. In many such diseases, the defect often does not involve the absence of a certain gene; it involves the presence of a gene with an altered nucleotide sequence, such as substituted or missing nucleotides, but which otherwise is identical to a normal gene. In FIG. 4, the defective nucleotide sequence in chromosomal gene 124 is indicated by the minus "−" sign and the callout number 126. The goal of the gene therapy procedure is to replace defective nucleotide sequence 126 with a properly functioning nucleotide sequence 38 (indicated by the plus "+" sign in FIG. 4) located in the dsDNA 32 of the rDNA component 30.

In one preferred embodiment which maximizes the nucleotide sequence homology between the rDNA component 30 and a defective human chromosomal gene 124, any bacterial, viral, non-homologous eukaryotic, or other non-human dsDNA which is not homologous with the defective chromosomal gene 124 is omitted from the rDNA component 30. This minimizes unwanted foreign gene expression or recombination. In addition, the PLR molecule 50 is used without other cotransfected dsDNA, since the latter can compete with and thereby lower the overall transfection frequency (Green et al 1991).

Therefore, the specific and proximal positioning of the PLR molecule 50 due to the dsDNA-binding polypeptide (P) component 10, the flexible extension contributed by the linker (L) component 20, and the size, structure, and nucleotide sequence homology of the rDNA (R) component 30, all contribute to facilitating the site-specific replacement of a defective chromosomal sequence 126 by a portion of the rDNA containing the desired gene sequence 38. The result of this polypeptide-linked recombination (PLR) process is a chromosomal recombinant 124A, shown in the lower portion of FIG. 4, having a properly functioning structural nucleotide sequence 38.

If the regulatory nucleotide sequences 122 of the gene 124 are functioning properly and do not require replacement, they will remain unchanged. No regulatory nucleotide sequences would be present in the rDNA component 30 of the PLR molecule 50, and no alteration would be made to the chromosomal regulatory sequences during the PLR process.

The dsDNA-binding polypeptide 10 which binds to nucleotide sequence 122 will eventually become unbound from the chromosome 120 (McKay et al 1981; Arfin and Bradshaw 1988). In this invention, the reacted PLR molecule 50A will therefore be degraded by natural cellular processes.

If desired, an rDNA component can contain defective or chemically modified nucleotide sequences, in order to perform site-specific mutagenesis. Furthermore, specific regulatory nucleotide sequences could be included in a rDNA component, in order to correct or mutagenize the corresponding or nearby chromosomal sequences. An rDNA of this type, or a natural or altered polypeptide component, can also be used to deliberately interact with polypeptide components of other PLR molecules or with other intracellular polypeptides, in order to extend their effectiveness along a chromosome or to otherwise affect selected intracellular functions, such as replication, recombination, gene regulation, and repair of mutations which involve polypeptide-nucleic acid, and polypeptide-polypeptide interactions (Lewin 1990).

The crosslinking reaction may generate an assortment of conjugated structures (i.e., DNA segments can be coupled to any lysine or certain other residues that may provide amino groups accessible on the surface of the polypeptide). Accordingly, this crosslinked mixture may contain some conjugates that will not perform effectively. However, the presence of some ineffective conjugates in such a mixture will not prevent conjugates with the proper structure from effectively transfecting cells. Due to the nature of the impediments created by DNA segments bound to inappropriate residues on the polypeptides, such ineffective conjugates should not be toxic or lethal to cells. If the NLS sequence of a conjugated polypeptide is blocked, the conjugate will simply remain in the cytoplasm, unable to enter the nuclei, or it might not enter a cell at all. In either case, it will not kill the cells, but will simply remain in the cytoplasm or extracellular fluid until degraded or removed. Similarly, if the chromosome-binding portion of a conjugated peptide is blocked by a crosslinked DNA segment, the conjugate might be able to enter the nucleus, but it will not be able to bind to a chromosomal binding site, and it will simply remain inside the nucleus until it is eventually degraded.

In either case, a mixture of conjugates created as described herein will be effective and useful if it contain at least some conjugates in which the DNA segment does not interfere with the NLS or chromosomal binding portion of the polypeptide.

In addition, if desired, any of several techniques can be used to enrich or purify conjugates having the desired configurations, in which the NLS and chromosome-binding portions are not hindered. As one example of such a technique, isolated NLS domains and chromosomal binding domains can be synthesized and injected into mice or rabbits, to generate monoclonal or polyclonal antibody preparations that bind only to the NLS domains; synthetic affinity-binding peptide fragments could also be created and used. Such antibody or binding fragment preparations could be used in either of two manners:

(1) the antibodies or binding fragments can be affinity-bound to the NLS domains of the chromosome-binding polypeptides before the crosslinking reaction. This would effectively block and thereby protect the NLS domains during the crosslinking reaction. After the covalent crosslinking reaction has been completed, the conditions are altered to release the affinity-bound antibodies or fragments from the polypeptide.

(2) the antibodies or binding fragments can be immobilized in an affinity column. After crosslinking of the chromosome-binding polypeptides to the DNA segments, the conjugates could be passed through the affinity column. Only those conjugates having a desired configuration, with unblocked NLS domains, would be retained in the column, while undesired conjugates would pass through. After removal of the undesired conjugates, the column conditions can be altered to release the desired conjugates.

In a similar manner, the chromosome-binding sites of sequence-specific chromosome-binding polypeptides can be protected, during a crosslinking reaction, by incubating the polypeptides with synthetic DNA fragments having the sequences that the polypeptides will bind to. After the crosslinking reaction is finished, the conditions are altered to release the DNA fragments from the polypeptides.

In still another alternate approach, a chromosome-binding polypeptide can be given more than one NLS sequence if desired, by creating a fusion protein that has the endogenous NLS sequence along with an additional NLS sequence derived from an SV40 virus or any of various other sources. Since the crosslinking reaction preferably should be carried out using a molar excess of peptide with a limited amount of crosslinking agent or DNA (as described on pages 37–38 of the specification), it would be highly unlikely that both of the NLS sequences in the peptide would be blocked by DNA segments.

Such processing steps probably will not be required for most transfections; ineffective conjugates will simply be harmless byproducts, and the appropriately structured conjugates that are present in the mixture will be sufficient for transfecting cells. However, an additional processing step as outlined above may improve yields, so it can be carried out if economically advantageous, or if a particular gene appears to be intractable to stable transfection unless such additional processing is used.

In some situations, the addition of a cofactor (such as a glucocorticoid hormone) which induces or increases the transcription of a particular target gene, or a mitogen to stimulate cell division, may be able to increase the frequency of desired PLR-mediated recombination events for some genes, since transcription or replication may increase the accessibility of a gene sequence for a chromosome-binding polypeptide. In such situations, such cofactors or mitogens can be provided in any of several ways, such as by adding them directly to the culture medium, or by inducing transcription of certain genes or using recombinant expression vectors to increase cellular synthesis of such cofactors.

Identification and Selection of Transfected Cells

The presence of the newly-acquired DNA sequence 32, and its stability, location, and proper functioning in the cell chromosomes, can be evaluated in various ways. For example, tests which can identify dsDNA sequences, using transfected cells or their progeny, can be performed using the polymerase chain reaction methodology described in patents such as U.S. Pat. No. 4,683,202 (Mullis et al) and in articles such as Erlich et al 1991 and Ehlen and Dubeau 1989, and by a related process known as the ligase chain reaction (Barany et al 1991). These tests also allow for the comparison and further development of techniques involving the transfection conditions, recipient cell types, PLR molecule and reagent concentrations, buffers, etc. Tests such as Southern blotting involving transfected cells, or progeny cells derived therefrom, can indicate whether the portion of the transfected DNA has remained site-specifically recombined into the specific chromosomal site (Sambrook et al 1989). Nucleotide sequencing can further indicate whether the original nucleotide sequence of the homologously recombined DNA segment, and also the flanking chromosomal sequences, have remained intact (Owens et al 1991).

One example of an indicator gene which identifies transfected cells is the lacZ gene from bacteria, which causes transfected mammalian cells to express a blue color when they are grown in nutrient media containing the substrate 5-bromo-4-chloro-3-indolyl-beta-D-galactopyranoside (i.e., X-gal); see Lim and Chae 1989. In addition, methods are available for using techniques such as flow cytometry and cell sorting to identify and select transfected cells, particularly if the transfected cells express a new polypeptide bound by an antibody on the cell surface (Jasin et al 1990).

To select for transfected cells, the rDNA component 30 can contain a selectable marker if desired. As an example of a selectable marker, the prokaryotic xanthine-guanosine-phosphoribosyltransferase (XGPRT) gene, when transfected into mammalian cells, allows the cells to survive in the presence of mycophenolic acid, an inhibitor of guanosine monophosphate synthesis.

Two different selectable markers, such as the prokaryotic neomycin (neo) gene and the herpes virus thymidine kinase (tk) gene, can also be included as part of the rDNA component 30. The neo gene confers resistance to the cytotoxic drug G418, while the tk gene confers sensitivity to the cytotoxic drug gancyclovir. The neo marker should be located centrally in the rDNA segment 32 while the tk marker(s) should be located near one or both termini. When cells are grown in the presence of both drugs, non-transfected cells, and transfected cells which do not retain the rDNA segment 32, are both killed by the drug G418, since they do not have the neo gene. Transfected cells which have retained the neo gene and also the terminal rDNA segment(s) in the chromosome, including the tk drug-sensitivity marker, are killed by gancyclovir. Only those transfected cells which have retained the central portion of the rDNA, including the neo marker but not the tk marker, will survive and thereby be enriched. These surviving cells generally comprise homologous recombinants, while the killed cells containing the tk marker generally comprise non-homologous recombinants (Capecchi et al 1989).

All of the above methods discussed in the prior art can thus identify transfected cells or select for homologous recombinants, but they were not designed for increasing the frequency of homologous recombinants. By contrast, an increased frequency of homologous recombination events can be enabled by using the PLR molecule, which can also include all of the selectable and indicator genes and methods discussed above.

Method of Controlling the Time of Nuclear Entry

This invention also discloses a method of controlling the time during which PLR molecules are allowed to migrate from the cytoplasm and enter the nucleus of a transfected cell. This method enables PLR molecules to enter the nucleus during a selected portion of the cell cycle, or to coincide with other natural or experimental conditions, in which the target gene is about to be or is already replicating or being transcribed. At these times, replicating or transcribed genes can be more physically accessible for binding by sequence-specific polypeptides (see Felsenfeld 1992) and the efficiency of homologous recombination at such genes can also be increased (Wong and Capecchi 1987; Goldman 1988; Hatton et al 1988).

The time for nuclear entry can be controlled by coupling a ligand (such as a fluorescein group) to sufficient PLR molecules, preferably at the NLS domain of the chromosome-binding polypeptides. The ligand-PLR molecules are then transfected into cells, as described above, along with an antibody which can bind to the ligand in the cytoplasm. This antibody binding can sterically hinder the NLS of the ligand-PLR molecules, thereby inhibiting their entry into the nuclei of transfected cells. For a number of types of genes, analysis can indicate when the target gene is suitably accessible for sequence-specific polypeptide binding and homologous recombination (such as when the cells are treated with a hormone or other transcription-inducing compound, in the case of inducible genes, or during an appropriate phase of the cell cycle). At the appropriate time, the cells are treated with ligands (such as 5-aminofluorescein) which will bind in a competitive manner to the antibodies, thereby freeing the ligand-PLR molecules to migrate from the cytoplasm and enter the nuclei. The coupling of a ligand to an NLS-containing polypeptide, and the use of an anti-ligand antibody and a competitively binding ligand, to control the cytoplasmic residence time of polypeptides with NLS sequences, was described in Halleck and Rechsteiner 1990, and could be adapted for use with a PLR molecule as described herein.

Organelle Transfection

This invention also suggests a method of transfecting organelles such as mitochondria and chloroplasts. Chloroplast genes in plant cells are involved in herbicide resistance (Sugiura 1989), and in humans, defective mitochondrial genes can cause genetic diseases (diMauro et al 1985). Organelle-specific dsDNA-binding polypeptides are transported into the proper organelles with the aid of mitochondrial localization sequences or chloroplast localization sequences, which function in a manner comparable to nuclear localization sequences (Fisher 1989). Therefore, organelle-specific dsDNA-binding polypeptides may be useful for organelle transfection, in a manner comparable to the use of nuclear dsDNA-binding polypeptides as described herein.

Commercial and Pharmaceutical Uses

In addition to the replacement of defective genes and site-specific mutagenesis for various medical and industrial purposes (and for research purposes as well, although research use is subject to the "experimental use exception" which provides that many forms of research do not infringe patent rights), this invention can also involve rDNA components containing genes which are valuable for expression in eukaryotic or prokaryotic cell culture or in intact eukaryotic organisms. For example, goats and cows can be transfected with a gene that causes the expression of a desired polypeptide in the milk. The polypeptide can be isolated from the milk by means of various processing techniques (Wright et al 1991). All of the prior art efforts used to accomplish those goals have used transfection methods which cannot efficiently transport the recombinant DNA to an actively-transcribing chromosomal site; therefore, genetic expression of the transfected DNA is often low. In addition, under the prior art, the transfection into chromosomal sites is not sequence specific; this can inactivate essential genes and cause other unwanted genetic effects, as described in the Background section.

By contrast, this invention offers a method of efficiently transfecting rDNA segments into chromosomal sequences which are often referred to as non-essential sequences, since they either cannot encode polypeptides, or the polypeptides have no known natural function (Weiner et al 1986). One example of such sequences includes highly repetitive DNA sequences that are present in all mammalian cells (see Lewin 1990) and a human dsDNA-binding polypeptide has been reported which binds to such repetitive DNA sequences (Chesnokov 1991). This polypeptide (or a functionally similar polypeptide) could be used as the polypeptide component of a PLR molecule. Following transfection, the rDNA component can be recombined, either with or without relying on homologous recombination, into one or more of the repetitive sequences.

If homologous recombination is desired, the rDNA component of the PLR conjugate can also incorporate a coding or non-coding nucleotide sequence which is homologous to a repetitive or other type of chromosomal sequence. This can increase genetic expression and reduce unwanted integration into essential genes. Even if homologous recombination is not relied upon, coupling the rDNA sequence to a dsDNA-binding polypeptide will still enable efficient transport into the nucleus and binding of the PLR molecule on a chromosome, thereby increasing the frequency of the desired non-homologous integration into the chromosome.

This method, and the components of the PLR molecule 50 created by such method, have a number of important advantages and valid uses over the prior art, including:

(1) they can facilitate the structural stability of the transfected PLR molecule in the cytoplasm and nucleus;

(2) they can facilitate the transport of the PLR molecule from the cytoplasm into the nucleus;

(3) they can facilitate the contact, translocation, and site-specific binding of the PLR molecule on a specified chromosomal gene;

(4) they can facilitate the site-specific recombination of their own genomic DNA or complementary DNA (cDNA) into a specified eukaryotic gene;

(5) they need not contain foreign (e.g., bacterial, viral, non-homologous eukaryotic, or other non-human) DNA;

(6) they can be constructed and purified precisely, safely, and reproducibly;

(7) the final product can be tested for efficient and safe therapeutic use by using standard biochemical assays, tissue culture cells, or laboratory animals;

(8) they can be used with a variety of transfection methods;

(9) they can be used for the transfection of a large variety of genes, and for several genes simultaneously;

(10) they can be used to transfect a wide variety of eukaryotic cell types;

(11) they can enable improved site-specific mutagenesis in human and other eukaryotic cells for industrial research;

(12) they can facilitate the industrial synthesis of polypeptides by human or other eukaryotic cells; and,

(13) they can enable improved and effective gene therapy for defective chromosomal genes of man and other eukaryotes.

Thus there has been shown and described a new composition of matter and a method for site-specifically transfecting eukaryotic cells. Although this invention has been exemplified for purposes of illustration and description by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by this invention, which is limited only by the claims below.

REFERENCES

Ackerman, S. L., et al, *Proc. Natl. Acad. Sci. USA* 90: 11865–11869 (1993)

Alberts, B., et al., *The Molecular Biology of the Cell,* 2nd ed. (Garland Publ., N.Y., 1989)

Anjaneyulu, P. S. R., and Staros, J. V., *Int. J. Peptide Protein Res.* 30: 117–124 (1987)

Arfin, S. M., and Bradshaw, R. A., Biochem. 27: 7979-7984 (1988)

Baim, S. B., et al, *Proc. Natl. Acad. Sci. USA* 88: 5072–5076 (1991)

Barany, F., *Proc. Natl. Acad. Sci. USA* 88: 189–193 (1991)

Baumhueter, T., et al, *Genes Dev.* 2: 1400–1413 (1988)

Bayer, E. A., et al, *Biochem.* 29: 11274–11279 (1990)

Beato, M., *Cell* 56: 335–344 (1989)

Beckmann, H., et al, *Genes Dev.* 4: 167–179 (1990)

Berkner, K. L., *Biotechniques* 6: 616–629 (1988)

Bianchi, M. E., et al, *Science* 243: 1056–1059 (1989)

Bodner, M., et al, *Cell* 55: 505–518 (1988)

Bowerman, B., et al., *Genes and Development* 3: 469–478 (1989)

Briggs, M. R., et al., *Science* 234: 47–52 (1986)

Capecchi, M. R., *Science* 244: 1288–1292 (1989)

Cheng, S. T., et al., *Nucl. Acids Res.* 11: 659–669 (1983)

Chesnokov, I., et al, *Biochem. Biophys. Res. Commun.* 178: 613–619 (1991)

Chiang, X. -B., and Wilson, J. H., *Proc. Natl. Acad. Sci. USA* 84: 4959–4963 (1987)

Davis, T. L., et al, *Proc. Natl. Acad. Sci. USA* 86: 9682–9688 (1989)

Deng, C. and Capecchi, M. R., *Mol. Cell. Biol.* 12: 3365–3371 (1992)

Dignam, J. D., et al, *Methods Enzymol* 101: 582–598 (1983)

diMauro, S., et al, *Ann. Neurol.* 17: 521–538 (1985)

Eglitis, M. A. and Anderson, W. F., *Biotechniques* 6: 608–614 (1988)

Ehlen, T. and Dubeau, L., *Biochem. Biophys. Res. Commun.* 160: 441–447 (1989)

Elder, G. A., et al, *Nucl. Acids Res.* 20: 6281–6285 (1992)

Erlich, H. A., et al, *Science* 252: 1643–1651 (1991)

Fallon, R. A., and Malcolm, D. B., *Biochem. Soc. Trans.* 13: 367–368 (1985)

Fan, C. M., and Maniatis, T., *Genes Dev.* 4: 29–42 (1990)

Feldherr, C. M. and Dworetzky, S. I., *Cell Biol. Int. Rep.* 12: 791–808 (1988)

Felsenfeld, G., *Nature* 355: 219–224 (1992)

Ferrari, S., et al, *EMBO J.* 11: 4497–4506 (1992)

Fisher, R. P., et al, *Genes Dev.* 3: 2202–2217 (1989)

Frain, M., et al, *Cell* 59: 145–157 (1989)

Friedmann, T., *Science* 244: 1275–1281 (1989)

Gasser, S. M., and Laemmli, U. K., *Trends Genet.* 3: 16–22 (1987)

Gilmour, D. S. and Lis, J. T., *Mol. Cell. Biol.* 5: 2009–2018 (1985)

Ginsberg, H. S., et al, *Proc. Natl. Acad. Sci. USA* 88: 1651–1655 (1991)

Gloss, B. and Bernard, H. -U., *J. Virol.* 64: 5577–5584 (1990)

Goldman, M. A., *Bioessays* 9: 50–55 (1988)

Green, M. H. L., et al, *Exp. Cell Res.* 192: 298–301 (1991)

Green, N. M., *Advan. Prot. Chem.* 29: 85–133 (1975)

Halleck, M. S. and Rechsteiner, M. R., *Proc. Natl. Acad. Sci. USA* 87: 7551–7554 (1990)

Hartl, F. -U. and Newpert, W., *Science* 247: 930–938 (1990)

Hatton, K. S., et al, *Mol. Cell. Biol.* 8: 2149–2158 (1988)

Jablonski, J., et al, *Nucl. Acids Res.* 14: 6115–6128 (1986)

Janknecht, R. and Nordheim, A., *Biochim. Biophys. Acta* 1155: 346–356 (1993)

Jantzen, H. -M., et al, *Nature* 344: 830–836 (1990)

Jasin, M. S., et al, *Genes Dev.* 4: 157–166 (1990)

Johnson, P. F. and McKnight, S. L., *Ann. Rev. Biochem.* 58: 799–839 (1989)

Kageyama, R. and Pastan, I., *Cell* 59: 815–825 (1989)

Kemler, I., et al, *EMBO J.* 8: 2001–2008 (1989)

Keown, W. A., et al, *Methods in Enzymology* 185: 527–537 (1990)

King, C. -Y. and Weiss, M. A., *Proc. Natl. Acad. Sci. USA* 90: 11990–11994 (1993)

Klein, T. M., et al, *Nature* 327: 70–73 (1987)

Klemsz, M. J., et al, *Cell* 61: 113–124 (1990)

Kutoh, E., and Schwander, J., *Biochem. Biophys. Res. Commun.* 194: 1475–1482 (1993)

Landschulz, W. H., et al., *Genes and Development* 2: 786–800 (1988)

LeMaitre, M., et al, *Proc. Natl. Acad. Sci. USA* 84: 648–652 (1987)

LeMarchand, P., et al, *Proc. Natl. Acad. Sci. USA* 89: 6482–6486 (1992)

Lewin, B., *Genes,* 4th ed. (Oxford University Press, N.Y., 1990)

Lim, K., and Chae, C. B., *Biotechniques* 7: 576–579 (1989)

Lyu, P. C., et al, *Proc. Natl. Acad. Sci. USA* 88: 5317–5320 (1991)

Mahler, H. R. and Cordes, E. H., *Biological Chemistry,* 2nd ed. (Harper and Row, N.Y. 1971)

Mannino, R. J. and Gould-Fogerity, S., *Biotechniques* 6: 682–690 (1988)

Mattaj, I. W. and DeRobertis, E. M., *Cell* 40: 111–118 (1985)

McKay, R. D. G., *J. Mol. Biol.* 145: 471–488 (1981)

McLachlin, J. R., et al., *Prog. Nucl. Acid Res. Mol. Biol.* 38: 91–135 (1990)

Merika, M. and Orkin, S. H., *Mol. Cell. Biol.* 13: 3999–4010 (1993)

Mitchell, P. J., and Tjian, R., *Science* 243: 371–378 (1988)

Nishizawa, M., et al, *FEBS Letters* 282: 95–97 (1991)

O'Neil, K. T., et al, *Science* 249: 774–778 (1990)

Oser, A., et al, *Anal. Biochem.* 191: 295–301 (1990)

Owens, J. D., et al, *Mol. Cell Biol.* 11: 5660–5670 (1991)

Parameswaran, K. N., et al, *Proc. Natl. Acad. Sci. USA* 87: 8472–8475 (1990)

Partis M. D., et al, *J. Prot. Chem.* 2: 263–277 (1983)

Peters, R., *Biochem. BioPhys. Acta* 864: 305–359 (1986)

Picard, D. and Yamamoto, K., *EMBO J.* 6: 3333–3340 (1987)

Plumb, M., et al, *Nucl. Acids Res.* 17: 73–92 (1989)

Ptashne, M., and Gann, A. A. F., *Nature* 346: 329–331 (1990)

Rabek, J. B., et al., *Nucl. Acids Res.* 18: 6677–6682 (1990)

Rauth, S., et al, *Proc. Natl. Acad. Sci. USA* 83: 5587–5591 (1986)

Razin, S. V., et al, *Proc. Natl. Acad. Sci. USA* 88: 8515–8519 (1991)

Renz, M., *EMBO J.* 2: 817–822 (1983)

Rubnitz, J. and Subramani, S., *Mol. Cell. Biol.* 4: 2253–2258 (1984)

Sagi, J., et al, *Nucl. Acids Res.* 18: 2133–2140 (1990)

Sambrook, J., et al., *Molecular Cloning: A Laboratory Manual,* 2nd ed. (Cold Spring Harbor Press, Cold Spring Harbor, N.Y., 1989)

Santoro, I. M., et al, *Mol. Cell. Biol.* 11: 1944–1953 (1991)

Singh, H., et al., *Biotechniques* 7: 252–261 (1989)

Smith, D. B. and Johnson, K. S., *Gene* 67: 31–40 (1988)

Stanbury, J. R., et al., eds., *The Metabolic Basis of Inherited Disease,* 9th ed. (McGraw-Hill, N.Y., 1983)

Staros, J. V., et al., *Methods in Enzymology* 150: 223–240 (1987)

Suguira, M., *Ann. Rev. Cell Biol.* 5: 51–70 (1989)

Suslick, K. S., *Science* 247: 1439–1447 (1990)

Thanos, D., and Maniatis, T., *Cell* 71: 777–789 (1992)

Towler, D. A., et al, *Ann. Rev. Biochem.* 57: 69–99 (1988)

Trainor, C. D., et al, *Nature* 343: 92–96 (1990)

Van der Wetering, M., et al, *EMBO J.* 10: 123–132 (1991)

Vestweber, D. and Schatz, G., *Nature* 338: 170–172 (1989)

Vollhardt, K. P. C., *Organic Chemistry* (W. H. Freeman and Co., NY, 1987)

von Kries, J. P., et al, *Cell* 64: 123–135 (1991)

Weiner, A. M., et al, *Ann. Rev. Biochem.* 55: 631–661 (1986)

Whyatt, D. J., et al, *EMBO J.* 12: 4993–5005 (1993)

Wilkison, W. O., et al, *J. Biol. Chem.* 265: 477–482 (1990)

Windgender, E., *Nucl. Acids Res.* 16: 1879–1902 (1988)

Wong, E. A. and Capecchi, M., *Mol. Cell. Biol.* 7: 2294–2295 (1987)

Wright, G., et al, *Biotechnology* 9: 830–838 (1991)

Zelenin, A. V., et al, *FEBS Letters* 280: 94–96 (1990)

Zinn, K. and Maniatis, T., *Cell* 45: 611–618 (1986)

Zuckermann, R. N., and Schultz, P. G., *J. Amer. Chem. Soc.* 110: 6592–6594 (1988)

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10 base pairs (B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: binding site for NF-KB chromosome binding
protein
(B) STRAIN: human
(F) TISSUE TYPE: human
(G) CELL TYPE: human (x) PUBLICATION INFORMATION:
(A) AUTHORS: Singh, H.
et al,
(C) JOURNAL: Biotechniques
(E) ISSUE: 7
(F) PAGES: 252-261
(G) DATE: 1989

(xi) SEQUENCE DESCRIPTION: SEQ ID NO:1:

GGGAAATTCC                                                                                                10

(2) INFORMATION FOR SEQ ID NO:2:

(i) SEQUENCE CHARACTERISTICS:
(A) LENGTH: 13 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: binding site for HNF1 chromosome binding
protein
(B) STRAIN: human
(F) TISSUE TYPE: human
(G) CELL TYPE: human (x) PUBLICATION INFORMATION:
(A) AUTHORS: Gasser, S.M.
Laemmli, U.K.
(C) JOURNAL: Trends Genetics
(E) ISSUE: 3
(F) PAGES: 16-22
(G) DATE: 1987

(xi) SEQUENCE DESCRIPTION: SEQ ID NO:2:

GTTAATNATT AAC                                                                                            13

(2) INFORMATION FOR SEQ ID NO:3:

(i) SEQUENCE CHARACTERISTICS:
(A) LENGTH: 15 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: binding site for topoisomerase II

```
                      chromosome binding protein
           ( B ) STRAIN: human
           ( F ) TISSUE TYPE: human
           ( G ) CELL TYPE: human ( x ) PUBLICATION INFORMATION:
           ( A ) AUTHORS: Baumhueter, T.
                          et al,
           ( C ) JOURNAL: Genes Dev.
           ( E ) ISSUE: 4
           ( F ) PAGES: 1400-1413
           ( G ) DATE: 1988

( x i ) SEQUENCE DESCRIPTION: SEQ ID NO:3:

G T N W A Y A T T N   A T N N R                                                                                    1 5
```

I claim:

1. A composition of matter comprising a preparation of molecular conjugates in which each molecular conjugate comprises a polypeptide component which is chemically bonded to a DNA segment, wherein the preparation of molecular conjugates is useful for in vitro genetic transformation of eukaryotic cells in a population of eukaryotic cells having a targeted chromosomal region, in a manner which replaces the targeted chromosomal region with a different DNA sequence contained in the preparation of molecular conjugates, wherein:

A) each polypeptide component comprises:
  (i) an amino acid sequence which functions as a nuclear localization sequence which enables migration of the molecular conjugate into a cell nucleus after the molecular conjugate has been inserted into a eukaryotic cell;
  (ii) an amino acid sequence which functions as a chromosome-binding domain which binds in a site-specific manner to a chromosomal binding site on a chromosome which contains the targeted chromosomal region inside the cell nucleus; and, B) the DNA segment in each molecular conjugate has nucleotide sequence homology with the targeted chromosomal region on the chromosome comprising the chromosomal binding site, which enables homologous recombination between the targeted chromosomal region and the DNA segment;

and wherein the preparation of molecular conjugates is useful under in vitro conditions, to genetically transform eukaryotic cells having the targeted chromosomal region, by means of steps comprising the following:
  (i) inserting the molecular conjugates into eukaryotic cells having the targeted chromosomal region, in an in vitro population of such cells;
  (ii) culturing the eukaryotic cells in vitro for a sufficient period of time to allow:
    (a) a nuclear localization sequence of a polypeptide component to transport a molecular conjugate into a cell nucleus;
    (b) a chromosome-binding domain of a polypeptide component to bind in a site-specific manner to a chromosome-binding domain in a chromosome in the cell nucleus; and,
    (c) homologous recombination between a DNA segment of a molecular conjugate and a targeted chromosomal region; and,
    (d) replication of genetically transformed cells in which the targeted chromosomal region has been replaced by a DNA sequence contained in the DNA segment of the molecular conjugate; and,
  (iii) identifying and selecting genetically transformed cells, or cells descended therefrom, in which the targeted chromosomal region has been replaced by a DNA sequence carried by the molecular conjugates.

2. The preparation of molecular conjugates of claim 1, wherein the DNA segment of the conjugates comprises a marker gene which facilitates identification and selection of treated cells and descendants thereof which contain the marker gene integrated into their chromosome s.

3. The preparation of molecular conjugates of claim 2, wherein the marker gene comprises a selectable marker gene that allows genetically transformed cells to reproduce under conditions in which untransformed cells cannot reproduce.

4. The preparation of molecular conjugates of claim 2, wherein the marker gene allows genetically transformed cells to convert a selected substrate into a different color that is not normally generated by untransformed cells.

5. The preparation of molecular conjugates of claim 2, wherein the marker gene causes genetically transformed cells to express a protein that is not normally expressed by untransformed cells.

6. The preparation of molecular conjugates of claim 1, wherein the polypeptide components are chemically bonded to the DNA segments by covalently bonding an accessible primary amine nitrogen atom to a DNA segment, and covalently bonding the primary amine nitrogen atom to a polypeptide component.

7. The preparation of molecular conjugates of claim 6, wherein the primary amine nitrogen atom is covalently bonded to the polypeptide component by means of a chemical crosslinking reaction which uses a crosslinking molecule having two reactive N-sulfosuccinimidyl ester groups.

8. A composition of matter comprising a preparation of molecule conjugates in which each molecular conjugate, comprises a polypeptide component which is chemically bonded to a DNA segment, wherein the molecular conjugate enables in vitro genetic transformation of a population of targeted eukaryotic cells which have a chromosome inside a cell nucleus containing (a) a known chromosomal binding site which interacts in a site-specific manner with a known DNA-binding polypeptide having a known amino acid sequence, and (b) a targeted chromosomal DNA sequence which is intended to be replaced by a different DNA sequence carried by the DNA segment of the molecular conjugate, wherein:
  (a) the polypeptide component of the molecular conjugate comprises an amino acid sequence which functions as a nuclear localization sequence which enables migration of the molecular conjugate into the cell nucleus after the molecular conjugate has been inserted into a eukaryotic cell;

(b) the polypeptide component also comprises an amino acid sequence which binds in a site-specific manner to the known chromosomal binding site on the chromosome inside the cell nucleus;

(c) the DNA segment of the molecular conjugate comprises a first gene sequence which has nucleotide sequence homology with the targeted chromosomal DNA sequence, which enables homologous recombination between the targeted chromosomal DNA sequence and the DNA segment of the molecular conjugate;

(d) the DNA segment of the molecular conjugate also comprises a second gene sequence which serves as a marker gene in cells which contain DNA from the molecular conjugate, integrated into their chromosomes in a stable and inheritable manner, and which actively express the marker gene.

9. The preparation of molecular conjugates of claim 8, wherein the marker gene comprises a selectable marker gene that allows genetically transformed cells to reproduce under conditions in which untransformed cells cannot reproduce.

10. The preparation of molecular conjugates of claim 8, wherein the marker gene allows genetically transformed cells to convert a selected substrate into a different color that is not normally generated by untransformed cells.

11. The preparation of molecular conjugates of claim 8, wherein the marker gene causes genetically transformed cells to express a protein that is not normally expressed by untransformed cells.

12. The preparation of molecular conjugates of claim 8, wherein the polypeptide components are chemically bonded to the DNA segments by covalently bonding an accessible primary amine nitrogen atom to a DNA segment, and covalently bonding the primary amine nitrogen atom to a polypeptide component.

13. The preparation of molecular conjugates of claim 12, wherein the primary amine nitrogen atom is covalently bonded to the polypeptide component by means of a chemical crosslinking reaction which uses a crosslinking molecule having two reactive N-sulfosuccinimidyl ester groups.

* * * * *